United States Patent [19]

De Boer et al.

[11] Patent Number: 5,756,417
[45] Date of Patent: May 26, 1998

[54] CATALYST COMPOSITIONS

[75] Inventors: Eric Johannes Maria De Boer, Amsterdam; Henricus Jacobus Robert De Boer, Hoofddorp; Hero Jan Heeres, Amsterdam, all of Netherlands

[73] Assignee: Union Carbide Chemicals & Plastics Technology Corporation, Danbury, Conn.

[21] Appl. No.: 792,259

[22] Filed: Jan. 31, 1997

Related U.S. Application Data

[62] Division of Ser. No. 284,946, Aug. 2, 1994, abandoned.

[51] Int. Cl.[6] ........................................ C08F 4/64
[52] U.S. Cl. .................. 502/117; 502/103; 502/152; 502/113; 556/20; 526/943
[58] Field of Search ...................... 502/103, 113, 502/117, 152; 556/20; 526/943

[56] References Cited

U.S. PATENT DOCUMENTS 5,434,116  7/1995  Sone et al. .............................. 502/103
5,504,172  4/1996  Imuta et al. ............................. 526/351

FOREIGN PATENT DOCUMENTS 0 574 794  12/1993  European Pat. Off. ........ C07F 17/00

OTHER PUBLICATIONS

Nief et al., *Journal of Organometallic Chemistry*, 384:271–278 (1990).

*Primary Examiner*—Mark Nagumo
*Attorney, Agent, or Firm*—P. W. Leuzzi

[57] ABSTRACT

Catalyst compositions for the oligomerization or polymerization of olefinically unsaturated hydrocarbons, comprising a heterocyclopentadienyl of the general formula $$C_4AR_4,$$

wherein A is a Group V element and each R, which is connected to a carbon of the heterocyclopentadienyl ring, can be the same or different and is chosen from hydrogen or an organic substituent (optionally containing one or more heteroatoms), in complex with a Group IV or V metal, and the process of oligomerization or polymerization olefinically unsaturated hydrocarbons in the presence of such catalyst compositions.

9 Claims, No Drawings

CATALYST COMPOSITIONS

This application is a division of prior U.S. application Ser. No. 08/284,946 filed Aug. 2, 1994, now abandoned.

FIELD OF THE INVENTION

This invention relates to catalyst compositions suitable for the oligomerization or for the polymerization of olefinically unsaturated hydrocarbons a Ziegler-Natta type catalysis, based on a Group IV or V metal complex and a cocatalyst.

BACKGROUND OF THE INVENTION

Ziegler-Natta catalysts have a long history. The first reports on homogeneous olefin polymerization catalysts composed of a Group IV metal complex and an alkylaluminum compound as cocatalyst were published by Breslow and Newburg (J. Am. Chem. Soc. 79 1957 5072 and 81 1959 81). Subsequently, it was reported that the addition of small amounts of water to the above compositions increased the rate of polymerization (W. P. Long, J. Am. Chem. Soc. 81 1959 5312; Long and Breslow, J. Am. Chem. Soc. 82 1960 1953). Later, Sinn and Kaminsky (e.g. in W. Kaminsky, Adv. Organometal Chemistry 18 1980 99) reacted the alkylaluminum with equimolar amounts of water to produce aluminoxane, which proved to be a much more effective cocatalyst. Currently, the best known aluminoxane cocatalyst is methyl aluminoxane (MAO). Still later, R. F. Jordan et al. (J. Am. Chem. Soc. 108 1986 1718 and 7410) replaced the cocatalyst by reacting the Group IV metal complex with a compound, the anion of which is substantially non-coordinating (protonation). K. Shelly and C. A. Reed (J. Am. Chem. Soc. 108 1986 3117) showed that the bulky carborate $B_{11}CH_{12}$ is "the least coordinating anion" and Turner (in EP-A 277003 and EP-A 277004) defined groups of bulky, substantially non-coordinating anions as cocatalysts with Group IV metallocene catalysts.

The Group IV metal compounds generally are metallocenes, containing in relation to the four valencies of the metal 1–4, in particular two, cyclopentadienyl ($C_5H_5$) rings, and 0–3, in particular also two, alkyl or halogen radicals. Several patent publications also claim similar Group V and VI metallocenes, in addition to the still preferred Group IV metallocenes.

In this specification, the term "olefinically unsaturated hydrocarbons" is often represented for convenience by "olefins".

Illustrative examples of patent publications relating to the more modern Ziegler-Natta catalysts and disclosing their use in the polymerization of olefins, in particular the production of solid, high-molecular polymers and copolymers of ethylene, are:

EP-B 69951 to HOECHST, disclosing catalyst compositions of bis(cyclopentadienyl)zirconium- dichloride or -methylchloride with methyl aluminoxane;

EP-B 129368 to EXXON, disclosing catalyst compositions of substituted mono-, bis- and tri(cyclopentadienyl)-Group IV metal halogenide or -hydrocarbide and an aluminoxane;

EP-A 277003 of EXXON, disclosing catalyst compositions of substituted or unsubstituted bis(cyclopentadienyl) Group IV metal hydrocarbide with an anion containing a plurality of boron atoms which is bulky, labile and capable of stabilizing the metal cation;

EP-A 277004 of EXXON, disclosing catalyst compositions of substituted or unsubstituted bis(cyclopentadienyl) Group IV metal hydrocarbide with an anion having a plurality of lipophylic radicals around a metal or metalloid ion, which anion is bulky, labile and capable of stabilizing the metal cation; and EP-A 426637 of FINA, disclosing a process for making catalyst compositions of substituted or unsubstituted bis (cyclopentadienyl) Group III–VI metal halogenide, hydrocarbide, amide or hydride with an anion which is non-coordinated or only loosely coordinated to the metallocene cation—by reacting the metallocene with a compound of said anion and carbonium, oxonium or sulfonium cation.

Illustrative examples of recent patent applications which are directed to similar catalyst compositions and which disclose in particular their use for the preparation of lower-molecular, liquid oligomers of ethylene and polymers of propylene, respectively are:

EP-A 596553 of SHELL, disclosing catalyst compositions of substituted bis(cyclopentadienyl) Group IV metal halogenide or hydrocarbide with a bulky, labile and substantially non-coordinating anion wherein the substitution of each of the two cyclopentadienyl radicals is different; and EP-A 540108 of SHELL, disclosing a catalyst composition of substituted bis(cyclopentadienyl) Group IV metal halogenide, hydrocarbyl, hydrocarbamide or hydride with aluminoxane wherein at least one cyclopentadienyl radical is substituted with a single optionally substituted aryl group.

It is to be noted that all of the above work used the cyclopentadienyl metal complexes, known under the general name of metallocenes. While most of the above identified publications, as well as further similar ones, contain in their scope substituents on the cyclopentadienyl ring, and while these substitutions in some cases may include one or more heteroatoms, the cyclopentadienyl ring itself remained unmodified.

SUMMARY OF THE INVENTION

It has now been found that by replacing the cyclopentadienyl ring of the known catalyst compositions as broadly described above with a substituted or unsubstituted heterocyclopentadienyl ring wherein the heteroatom is a Group V element, especially with such heterocyclopentadienyl rings which are substituted by a bulky substituent at one or both of the 2 and 5 positions, a new and exceedingly versatile group of Ziegler-Natta type catalysts can be made. Furthermore, the heterocyclopentadienyl-based catalysts were found to excel in producing a wide range of polymers (long, short and branched) from ethylene and olefins other than ethylene, and to be particularly efficient in the production of copolymers. Several of the heterocyclopentadienyl-based catalysts were found to be particularly useful in producing oligomers and short-chain polymers from alkenes, and syndiotactic polymers from styrene. Moreover, catalysts based on heterocyclopentadienyls as a group have a better thermal stability than cyclopentadienyl-based catalysts.

DETAILED DESCRIPTION OF THE INVENTION

The present invention relates to a catalyst composition for the oligomerization or polymerization of olefins. More particularly, the catalyst comprises a heterocyclopentadienyl of the general formula $C_4AR_4$, wherein A is a Group IV element and each R, which is connected to a carbon of the heterocyclopentadienyl ring, can be the same or different and is chosen from hydrogen or an organic substituent that optionally contains one or more heteroatoms, in complex with a Group IV or V metal. As used herein the terms oligomerization and polymerization are inclusive of "co-oligomerization" and "copolymerization."

The preferred Group V elements A in the present invention are phosphorus and nitrogen. The preferred heterocyclopentadienyl rings are the pyrrolyl rings, arsolyl rings, stibolyl rings, bismolyl rings, and phospholyl rings with phospholyl rings being preferred.

Preferably, one or both of the 2 and 5 positions on the heterocyclopentadienyl ring is substituted by a bulky substituent, i.e. a substituent wherein the atom directly attached to the ring is a group III, IV or V element (e.g. boron, carbon, silicon or nitrogen; with carbon or silicon being preferred), to which at least two atoms other than hydrogen are directly attached.

Illustrative examples of such bulky substituents are aryls such as phenyl, o-tolyl, p-t-Butylphenyl, m-dichlorophenyl and 3,5-t-Bu$_2$-4-MeOC$_6$H$_2$; secondary alkyls such as i-propyl, i-butyl and c-Pe (cyclopentyl); tertiary alkyls such as t-butyl; alkenyls such as —C(Me)=CH$_2$; and bulky substituents containing heteroatoms such as —SiMe$_3$, —NPh$_2$, —NHPh$_2$+, —BPh2 and —B(OPh)$_2$.

More preferably, none of the 2 and 5 positions on the heterocyclopentadienyl ring is unsubstituted. It is also preferred that the 3 and 4 positions on the heterocyclopentadienyl ring are not substituted by a bulky substituent.

The Group element notation in this specification is as defined in the Periodic Table of Elements according to the IUPAC 1988 notation (IUPAC Nomenclature of Inorganic Chemistry 1960, Blackwell Publ., London). Therein, Group IV, V, XIII, XIV and XV correspond respectively to Groups IVB, VB, IIIA, IVA and VA of the Deming notation (Chemical Rubber Company's Handbook of Chemistry & Physics, 48th edition) and to Groups IVA, VA, IIIB, IVB and VB of the IUPAC 1970 notation (Kirk-Othmer Encyclopedia of Chemical Technology, 2nd edition, Vol. 8,p. 94).

Illustrative examples of heterocyclopentadienyles according to the present invention are:
(3,4-Me$_2$C$_4$H$_2$P), (3,4-dimethylphospholyl)
(C$_4$Me$_4$P), (2,3,4,5-tetramethylphospholyl)
(C$_4$Me$_4$N), (2,3,4,5-tetramethylpyrrolyl)
(2,5-(CH$_3$)$_2$C$_4$H$_2$N), (2,5-dimethylpyrrolyl)
(C$_4$Me$_4$As), (2,3,4,5-tetramethylarsolyl)
[W(CO)$_4$ (C$_4$Me$_4$P)$_2$], [(-tungstentetracarbonyl) bis(2,3,4,5-tetramethylphospholyl)] and
[Fe(CO)$_3$(C$_4$Me$_4$P)$_2$], [(-irontricarbonyl) bis(2,3,4,5-tetramethylphospholyl)]

Illustrative examples of preferred heterocyclopentadienyles according to the invention are: (2,5-Ph$_2$C$_4$H$_2$P) 2,5-diphenylphospholyl; (2,5-c-Pe$_2$C$_4$H$_2$P) 2,5-dicyclopentylphospholyl; (2,5-i-Pr$_2$C$_4$H$_2$P) 2,5-diisopropylphospholyl; (2,5-t-Bu$_2$C$_4$H$_2$P) 2,5-ditertiarybutylphospholyl; (2,5-(Me$_3$Si)$_2$C$_4$H$_2$P) 2,5-ditrimethylsilylphospholyl; (2-Ph-5-MeC$_4$H$_2$P) 2-phenyl-5-methylphospholyl; (2-Ph-5-c-PeC$_4$H$_2$P) 2-phenyl-5-cyclopentylphospholyl; (2,5-Ph$_2$-3-MeC$_4$H$_2$P) 2,5-diphenyl-3-methylphospholyl; (2,4-Ph$_2$-3,5-Me$_2$C$_4$P) 2,4-diphenyl-3,5-dimethylphospholyl; (2-Ph-5-PrC$_4$H$_2$P) 2-phenyl-5-propylphospholyl; (2-Ph-5-PrC$_4$H$_2$P) 2-phenyl-5-propylphospholyl; (2-(3,5-t-Bu$_2$-4-OMeC$_6$H$_2$)-5-MeC$_4$H$_2$P) 2-(3,5-di-tertiarbutyl-4-methoxyphenyl)-5-methylphospholyl; 2-Ph-3,4-Me$_2$-5-(SiMe$_2$N-t-Bu) C$_4$P 2-phenyl-3,4-dimethyl-5-(dimethylsilyl-tertiarybutylamide) phospholyl; C$_{17}$H$_{12}$P which structure is provided in the experimental, compound XIV; dibenzo-2-methyl-1-phosphindolyl; C$_{20}$H$_{16}$N [a,i]dibenzo-3,4,5,6-tetrahydrocarbazolyl, structure provided in the experimental, compound XVII; C$_{22}$H$_{20}$N [a,i]di (methylbenzo)-3,4,5,6-tetrahydrocarbazolyl (2,5-t-Bu$_2$C$_4$H$_2$N) 2,5-ditertiarybutylpyrrolyl; (Ph$_4$C$_4$P) 2,3,4,5-tetraphenylphospholyl; 1,2-C$_2$H$_4$(3-PC$_8$H$_5$)$_2$ 1,2-ethylene-bis(3-phosphindolyl); Me$_2$Si(3-PC$_8$H$_5$)$_2$ dimethylsilylbis-(3-phosphindolyl); 1,2-C$_2$H$_4$(3-PC$_8$H$_9$)$_2$ 1,2-ethylene-bis (tetrahydro-3-phosphindolyl); Me$_2$Si(3-PC$_8$H$_9$)$_2$ dimethylsilylbis-(terahydro-3-phosphindolyl); 1,2-C$_2$H$_4$(3-PC$_{12}$H$_9$)$_2$ 1,2-ethylene-bis([benz]3-phosphindolyl); Me$_2$Si (3-PC$_{12}$H$_9$)$_2$ dimethylsilylbis-([benz]3-phosphindolyl); (C$_{12}$H$_8$P) 9-phosphafluorene; (C$_{18}$H$_{19}$P) 1-butyl-2-phenyl-3-phosphindolyl;

The heterocyclopentadienyles, C$_4$AR$_4$, according to the invention, when A is phosphorus, can be prepared as indicated by F. Mathey in Chem. Rev. 88 1988 429–453 and when A is arsenic or antimony they can be prepared in an analogous manner. In particular, C$_4$AsMe$_4$ was prepared by Ashe et al., Organometallics 11 1992 1491 and C$_4$PPh$_4$. C$_4$AsPh$_4$ and C$_4$SbPh$_4$ respectively were prepared by Braye et al., J. Am. Chem. Soc. 83 1961 4403, Braye et al., Tetrahedron 27 1971 5523 and Leavitt et al., J. Am. Chem. Soc. 82 1960 5099.

When A is nitrogen, the heterocyclopentadienyls C$_4$AR$_4$ can be prepared as described in Rodd's Chemistry of Carbon Compounds, 2nd Ed. Volume IV part A pages 329–345, Elsevier Publ. Amsterdam 1973.

In particular, the present invention relates to a catalyst composition for the oligomerization or polymerization of olefinically unsaturated hydrocarbons, comprising an organometal complex of the general formula

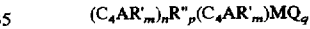

$$(C_4AR'_m)_nR''_p(C_4AR'_m)MQ_q$$

wherein A is a Group V element, each R', which can be the same or different, is chosen from hydrogen or an organic substituent having from 1 to 20 carbon atoms or two substituents together forming a fused C$_4$–C$_6$ ring, R" is a molecular fragment bridging two dienyl rings, M is a Group IV or V metal, each Q, which can be the same or different and two of which can be interconnected to form a ring, is hydrogen, aryl, alkyl, alkenyl, alkylaryl, arylalkyl, alkyloxyl, aryloxyl, alkylazanyl, arylazanyl, alkylthiolyl, arylthiolyl, alkylphosphalyl, arylphosphalyl, alkylazanediyl, arylazanediyl, alkylphosphanediyl, arylphosphanediyl, or cyclodienyl, any of which having from 1 to 20 carbon atoms and optionally being further substituted, or halogen, oxygen or sulphur, p is 0 or 1, m is 4 when p is 0, and 4 or 3 when p is 1, n is 0, 1, 2 or 3, q is 0, 1, 2 or 3 and n plus the sum of the valencies of the Q groups +1 equals the valency of the metal. Optionally, the organic substituent contains one or more heteroatoms.

The bridging molecular fragment R", when present, may be positioned between two carbon atoms of heterocyclopentadienyl rings, between a carbon and a hetero-atom A, or between two hetero-atoms A.

When R" is positioned between two carbon atoms it can be chosen from the wide range known for bridging two cyclopentadienyl, indenyl or fluorenyl rings, such as those disclosed in EP-B 129368, EP-A 336127 and EP-A 528287. Well-known examples thereof are the groups of C$_1$–C$_4$ radicals chosen from alkylene, dialkyl germanium or silicone, alkyl phosphine or amine and in particular 1,2-$C_2H_4$, 1,3-[$(CH_2)_3$], $(CH_3)_2Si$, $(CH_3)_2Si(O)_2$, 1,2-[$(CH_3)_2Si]_2$, 1,2-$(CH_2)_2C_6H_4$, $(CH_3)_2C$, 1,3-[{$(CH_3)_2Si$}$_2O$], 1,2-{$(CH_3)_2SiO$} and 1,3-[$(CH_3)_2Si(CH_2)_2$].

The use of the heterocyclopentadienyl rings according to the invention offers the unique possibility of varying the organometal complexes by involving the heteroatom in the bridge. In such cases, wherein R" is positioned between a carbon atom and a hetero-atom A or between two hetero-atoms A, care has to be taken to choose a fragment which is capable of making an electron donor-acceptor bond with A. Therefore, such bridges have to retain a Lewis acid site (to be coordinatively unsaturated). Metal fragments such as $W(CO)_4$ and $Fe(CO)_3$ have been shown to be suitable for this purpose. Bridging at the heteroatoms A by such fragments allows the heterocyclopentadiene ligand to act as a heterocyclopentadienyl anion for the Group IV or V metal.

Preferably, one or both of the 2 and 5 positions on the heterocyclopentadienyl ring is substituted by a bulky substituent. The term bulky substituent is intended in this specification to denote a substituent wherein the atom directly attached to the ring is a group 13, 14 or 15 element (e.g. boron, carbon, silicon or nitrogen, carbon or silicon being preferred), to which at least two atoms other than hydrogen are directly attached.

Illustrative examples of such bulky substituents are aryls such as phenyl, o-tolyl, p-t-Butylphenyl, m-dichlorophenyl and 3,5-t-$Bu_2$-4-$MeOC_6H_2$; secondary alkyls such as i-propyl, i-butyl and c-Pe (cyclopentyl); tertiary alkyls such as t-butyl; alkenyls such as —C(Me)=$CH_2$; and bulky substituents containing hetero-atoms such as —$SiMe_3$, —$NPh_2$, —$NHPh^+_2$, —$BPh_2$ and —$B(OPh)_2$.

More preferably, none of the 2 and 5 positions on the heterocyclopentadienyl ring is unsubstituted. It is also preferred that the 3 and 4 positions on the heterocycloentadienyl ring are not substituted by a bulky substituent.

The preferred metals M in the present invention are titanium, zirconium and hafnium.

The preferred Q radicals are hydrogen, methyl, ethyl, neopentyl, phenyl, benzyl and chloride.

The organometal complex according to the invention may contain from 1 to 4 of the above heterocyclopentadienyl rings, with from zero to three cyclopentadienyl rings and from zero to three (when the metal M is a Group IV metal: up to four) of the reactive groups Q which may react with the cation of the second component to form the complete catalyst composition. Therefore, organometal complexes containing only one heterocyclopentadienyl ring are expressly within the scope of the invention. However, organometal complexes containing two heterocyclopentadienyl rings, and those containing one such ring and one .cyclopentadienyl ring, are preferred.

The processing of the heterocyclopentadienyls to organometal complexes can be done along traditional synthesis routes. For example, the heterocyclopentadienyl anions can be prepared and reacted with zirconium tetrachloride to afford the bis-heterocyclopentadienyl zirconium dichlorides.

Illustrative examples of organometal complexes according to the invention are ($C_4Me_4P)_2ZrCl_2$, bis(2,3,4,5-tetramethylphospholyl) zirconium dichloride, ($C_4Me_4P)_2Zr(OCH_3)_2$, bis(2,3,4,5-tetramethylphospholyl) zirconium bismethoxide, ($C_4Me_4P)_2Zr(N(CH_3)_2)_2$, bis(2,3,4,5-tetramethylphospholyl) zirconium bis-dimethylamide, (3,4-$Me_2C_4H_2P)_2ZrCl_2$, bis(3,4-dimethylphospholyl) zirconium dichloride, ($C_4Me_4P$) ($C_5H_5$)$ZrCl_2$, (2,3,4,5-tetramethylphospholyl) (cyclopentadienyl) zirconium dichloride, ($C_4Me_4P$) ($C_5H_5$)$Zr(OCH_3)_2$, (2,3,4,5-tetramethylphospholyl) (cyclopentadienyl) zirconium bis-methoxide, ($C_4Me_4P$) ($C_5H_5$)$Zr(N(CH_3)_2$, (2,3,4,5-tetramethylphospholyl)-(cyclopentadienyl) zirconium bis-dimethylamide, (3,4-$Me_2C_4H_2P$) ($C_5H_5$)$ZrCl_2$, (3,4-dimethylpholyl) (cyclopentadienyl) zirconium dichloride ($C_4Me_4P)_2ZrMe_2$, bis(2,3,4,5-tetramethylphospholyl) zirconium dimethyl, ($C_4Me_4P)_2Zr${C(Ph)=C(Ph)—C(Ph)=C(Ph)}, bis(2,3,4,5-tetramethylphospholyl) 1-zircona-2,3,4,5-tetraphenylcyclopentadiene, ($C_4Me_4P)_2Zr${$CH_2CH_2CH_2CH_2$}, bis(2,3,4,5-tetramethylphospholyl) 1-zirconacyclopentane, ($C_4Me_4P)_2Zr(PhCCPh)$, bis(2,3,4,5-tetramethylphospholyl) zirconium tolane, (3,4-$Me_2C_4H_2P)_2ZrMe_2$, bis(3,4-dimethylphospholyl) zirconium dimethyl, ($C_4Me_4P$) ($C_5H_5$)$ZrMe_2$, (2,3,4,5-tetramethylphospholyl) (cyclopentadienyl) zirconium dimethyl, (3,4-$Me_2C_4H_2P$)($C_5H_5$)$ZrMe_2$, (3,4-dimethylphospholyl)(cyclopentadienyl) zirconium dimethyl, ($C_4Me_4P$)$ZrCl_3$, (2,3,4,5-tetramethylphospholyl) zirconium trichloride, (3,4-$Me_2C_4H_2P$)$ZrCl_3$, (3,4-dimethylphospholyl) zirconium trichloride, ($C_4Me_4P$)$ZrMe_3$, (2,3,4,5-tetramethylphospholyl) zirconium trimethyl, (3,4-$Me_2C_4H_2P$)$ZrMe_3$, (3,4-dimethylphospholyl) zirconium trimethyl, ($C_4Me_4P)_2TiCl_2$, bis(2,3,4,5-tetramethylphospholyl) titanium dichloride, ($C_4Me_4P)_2Ti${$CH_2C(Ph)HCH_2$}, bis(2,3,4,5-tetramethylphospholyl) 1-titana-3-phenyl-cyclobutane, ($C_4Me_4P)_2Ti${C(Ph)=C(Ph)HCH_2$}, bis(2,3,4,5-tetramethylphospholyl) 1-titana-2,3-diphenyl-cyclobutene, ($C_4Me_4P)_2Ti${$CH_2Si$ $(Me)_2CH_2$}, bis(2,3,4,5-tetramethylphospholyl) 1-titana-3-(dimethylsila)-cyclobutane, ($C_4Me_4P)_2TiCl$, bis(2,3,4,5-tetramethylphospholyl) titanium chloride ($C_4Me_4P$) ($C_5H_5$)$Ti(OCH_3)_2$, (2,3,4,5-tetramethylphospholyl) (cyclopentadienyl) titanium bis-methoxide, ($C_4Me_4P$) ($C_5H_5$) $TiOCH_3$, (2,3,4,5-tetramethylphospholyl) (cyclopentadienyl) titanium methoxide, ($C_4Me_4P$) ($C_5H_5$) $Ti(N (CH_3)_2)_2$, (2,3,4,5-tetramethylphospholyl) (cyclopentadienyl) titanium bis-dimethylamide, ($C_4Me_4P$) $TiCl_3$, (2,3,4,5-tetramethylphospholyl) titanium trichloride, ($C_4Me_4P$)$TiCl_2$, (2,3,4,5-tetramethylphospholyl) titanium dichloride, (3,4-$Me_2C_4H_2P$)$TiCl_3$, (3,4-dimethylphospholyl) titanium trichloride, ($C_4Me_4P$)$TiMe_3$, (2,3,4,5-tetramethylphospholyl) titanium trimethyl, (3,4-$Me_2C_4H_2P$)$TiMe_3$, (3,4-dimethylphospholyl) titanium trimethyl, [$W(CO)_4(C_4Me_4p)_2$]$ZrCl_2$, [(-tungstentetracarbonyl) bis(2,3,4,5-tetramethylphospholyl)] zirconium dichloride, [$Fe(CO)_3$ ($C_4Me_4P)_2$]$ZrCl_2$, [(-irontricarbonyl) bis(2,3,4,5-tetramethylphospholyl)] zirconium dichloride, ($C_4Me_4N)_2ZrCl_2$, bis(2,3,4,5-tetramethylpyrrolyl) zirconium dichloride, ($C_5(CH_3)_5$) (2,5-$(CH_3)_2C_4H_2N$) $ZrCl_2$, (pentamethylcyclopentadienyl) (2,5-dimethylpyrrolyl) zirconium dichloride, ($C_5(CH_3)_5$) (2,5-$(CH_3)_2C_4H_2N$) $ZrMe_2$, (pentamethylcyclopentadienyl) (2,5-dimethylpyrrolyl) zirconium dimethyl, ($C_4Me_4As$) ($C_5H_5$) $ZrCl_2$, (2,3,4,5-tetramethylarsolyl) (cyclopentadienyl) zirconium dichloride, [1,2-$C_2H_4$-(3,3'-(2,4,5-$Me_3C_4P)_2ZrCl_2$, 1,2-ethane-[3,3'-bis-(2,4,5-trimethylphospholyl)] zirconium dichloride, ($CH_3)_2Si(3,3'$-(2,4,5-$Me_3C_4P)_2ZrCl_2$, Dimethylsilane-[3,3'-bis(2,4,5-trimethylphospholyl)] zirconium dichloride ($C_6H_5)_2Si(3,3'$-(2,4,5-$Me_3C_4P)_2ZrCl_2$, Diphenylsilane-(3,3'-bis(2,4,5-trimethylphospholyl)] zirconium dichloride, [1,3-{$(CH_3)_2Si$}O](3,3'-(2,4,5-$Me_3C_4P)_2ZrCl_2$, 1,3-{bis-dimethylsilaneether}[3,3'-bis(2,4,5-trimethylphospholyl)] zirconium dichloride, 1,2-[$(CH_3)_2Si]_2$ (3,3'-(2,4,5-$Me_3C_4P)_2ZrCl_2$, 1,2-{bis-dimethylsilane}-[3,3'-bis(2,4,5-trimethylphospholyl)) zirconium dichloride [(C$_6$H$_5$)$_2$SiO$_2$](3,3'-(2,4,5-Me$_3$C$_4$P)$_2$ZrCl$_2$, {Diphenylsilanedioxyl}-[3,3'-bis(2,4,5-trimethylphospholyl)] zirconium dichloride (C$_4$Me$_4$P)V (NPh) Cl$_2$, (2,3,4,5-tetramethylphospholyl) (phenylimido) vanadium dichloride, (C$_4$Me$_4$N)$_3$TaCl$_2$, tris(2,3,4,5-tetramethylphospholyl) tantalum dichloride, (C$_4$Me$_4$P)$_2$VCl$_2$, bis(2,3,4,5-tetramethylphospholyl) vanadium dichloride, and (C$_4$Me$_4$P) VCl$_3$, (2,3,4,5-tetramethylphospholyl) vanadium trichloride.

Illustrative examples of preferred organometal complexes according to the invention are: (2,5-Ph$_2$C$_4$H$_2$P)$_2$ZrCl$_2$, bis (2,5-diphenylphospholyl) zirconium dichloride, (2,5-Ph$_2$C$_4$H$_2$P) (C$_5$H$_5$)ZrCl$_2$, (2,5-diphenylphospholyl) (cyclopentadienyl) zirconium dichloride, (C$_4$Ph$_4$P)$_2$ZrCl$_2$, bis(2,3,4,5-tetraphenylphospholyl) zirconium dichloride, (C$_4$Ph$_4$P)$_2$Zr(OCH$_3$)$_2$, bis(2,3,4,5-tetraphenylphospholyl) zirconium bis-methoxide, (C$_4$Ph$_4$P)$_2$Zr(N(CH$_3$)$_2$)$_2$, bis (2,3,4,5-tetraphenylphospholyl) zirconium bis-dimethylamide, (C$_4$Ph$_4$P) (C$_5$H$_5$)ZrCl$_2$, (2,3,4,5-tetraphenylphospholyl) (cyclopentadienyl) zirconium dichloride, (2,5-Ph$_2$C$_4$H$_2$P)$_2$ZrMe$_2$, bis (2,5-diphenylphospholyl) zirconium dimethyl, (2,5-Ph$_2$C$_4$H$_2$P) ZrMe$_3$, (2,5-diphenylphospholyl) zirconium trimethyl, (2,5-Ph$_2$C$_4$H$_2$P) (C$_5$H$_5$)ZrMe$_2$, (2,5-diphenylphospholyl) (cyclopentadienyl) zirconium dimethyl, (C$_4$Ph$_4$P)$_2$ZrMe$_2$, bis (2,3,4,5-tetraphenylphospholyl) zirconium dimethyl, (C$_4$Ph$_4$P) (C$_5$H$_5$)ZrMe$_2$, (2,3,4,5-tetraphenylphospholyl) (cyclopentadienyl) zirconium dimethyl, (2,5-Ph$_2$C$_4$H$_2$P) ZrCl$_3$, (2,5-diphenylphospholyl) zirconium trichloride, (2,5-Ph$_2$C$_4$H$_2$P) TiCl$_3$, (2,5-diphenylphospholyl) titanium trichloride, (2,5-Ph$_2$C$_4$H$_2$P)TiMe$_3$, (2,5-diphenylphospholyl) titanium trimethyl, (C$_4$Me$_4$P) (2,5-Ph$_2$C$_4$H$_2$P)ZrCl$_2$, (2,3,4,5-tetramethylphospholyl) (2,5-diphenylphospholyl) zirconium dichloride, (2-Me-5-PhC$_4$H$_2$P)$_2$ZrCl$_2$, bis (2-methyl-5-phenylphospholyl) zirconium dichloride, (2,5-t-Bu$_2$C$_4$H$_2$N)$_2$ZrCl$_2$, bis(2,5-di-t-butylpyrrolyl) zirconium dichloride, (C$_5$ (CH$_3$)$_5$) (2,5-(t-C$_4$H$_9$)$_2$C$_4$H$_2$N)ZrCl$_2$, (pentamethylcyclopentadienyl) (2,5-di-t-butylpyrrolyl) zirconium dichloride, (C$_5$(CH$_3$)$_5$) (2,5-(t-C$_4$H$_9$)$_2$C$_4$H$_2$N)ZrMe$_2$, (pentamethylcyclopentadienyl) (2,5-di-t-butylpyrrolyl) zirconium dimethyl, (2-Ph-5- (2-ClC$_6$H$_4$)C$_4$H$_2$P)$_2$ZrCl$_2$, bis (2-phenyl-5-o-chlorophenyl-phospholyl) zirconium dichloride, (2- (2-MeOC$_6$H$_4$)Me$_3$C$_4$P)ZrCl$_3$, 2-orthomethoxyphenyl-3,4,5-trimethylphospholyl zirconium trichloride, [1,2-C$_6$H$_4$-(2,2'-(5-PhC$_4$H$_2$P)$_2$]ZrCl$_2$, 1,2-phenyl-[2,2'-bis(5-phenylphospholyl)] zirconium dichloride, (C$_{17}$H$_{12}$P)$_2$ZrCl$_2$ bis (dibenzo-2-methyl-1-phosphindolyl) zirconium dichloride, (2-Ph-5-PrC$_4$H$_2$P)$_2$ZrCl$_2$ bis (2-phenyl-3-propylphospholyl) zirconium dichloride, 1,2-C$_2$H$_4$-(5,5'-(2-PhC$_4$H$_2$P)$_2$ZrCl$_2$, 1,2-ethane-(5,5-bis(2-phenylphospholyl) zirconium dichloride, 1,2-C$_2$H$_4$-(1,1'-(3-PC$_8$H$_5$)$_2$ZrCl$_2$, 1,2-ethane-(1,1-bis(3-phosphindolyl) zirconium dichloride, (C$_{17}$H$_{12}$P)$_2$ZrMe$_2$ bis (dibenzo-2-methyl-1-phosphindolyl) zirconium dimethyl, (2-Ph-5-PrC$_4$H$_2$P)$_2$ZrMe$_2$ bis (2-phenyl-5-propylphospholyl) zirconium dimethyl, 1,2-C$_2$H$_4$-(5,5'-(2-PhC$_4$H$_2$P)$_2$ZrMe$_2$ 1,2-ethane-(5,5'-bis(2-phenylphospholyl) zirconium dimethyl, 1,2-C$_2$H$_4$-(1,1'-(3-PC$_8$H$_5$)$_2$ZrMe$_2$ 1,2-ethane-(1,1'-bis(3-phosphindolyl) zirconium dimethyl, (C$_{12}$H$_8$P)$_2$ZrCl$_2$ Bis-(9-phosphafluorenyl) zirconium dichloride, (C$_{12}$H$_8$P)$_2$ZrMe$_2$ Bis-(9-phosphafluorenyl) zirconium dimethyl, (2,5-c-Pe$_2$C$_4$H$_2$P)$_2$ZrCl$_2$ bis-(2,5-dicyclopentylphospholyl) zirconium dichloride, (2,5-i-Pr$_2$C$_4$H$_2$P)$_2$ZrCl$_2$ bis-(2,5-diisopropylphospholyl) zirconium dichloride, (2,5-t-Bu$_2$C$_4$H$_2$P)$_2$ZrCl$_2$ bis-(2,5-ditertiarybutylphospholyl) zirconium dichloride, (2,5-(Me$_3$Si)$_2$C$_4$H$_2$P)$_2$ZrCl$_2$ bis-(2,5-di-trimethylsilylphospholyl) zirconium dichloride, (2-Ph-5-c-PeC$_4$H$_2$P)$_2$ZrCl$_2$ bis- (2-phenyl-5-cyclopentylphospholyl) zirconium dichloride, (2,5-Ph$_2$-3-MeC$_4$H$_2$P)$_2$ZrCl$_2$ bis-(2,5-diphenyl-3-methylphospholyl) zirconium dichloride, (2,4-Ph$_2$-3,5-Me$_2$C$_4$P)$_2$ZrCl$_2$ bis-(2,4-diphenyl-3,5-dimethylphospholyl) zirconium dichloride, (2-Ph-5-PrC$_4$H$_2$P)$_2$ZrCl$_2$ bis-(2-phenyl-5-propylphospholyl) zirconium dichloride, (2-(3,5-t-Bu$_2$-4-OMeC$_6$H$_2$)-5-MeC$_4$H$_2$P)$_2$ZrCl$_2$ bis-(2-(3,5-di-tertiarbutyl-4-methoxyphenyl)-5-methylphospholyl) zirconium dichloride, (2-(3,5-t-Bu$_2$-4-OMeC$_6$H$_2$)-5-MeC$_4$H$_2$P) (C$_5$H$_5$)ZrCl$_2$ (2-(3,5-di-tertiarbutyl-4-methoxyphenyl)-5-methylphospholyl) cyclopentadienyl zirconium dichloride, (C$_{17}$H$_{12}$P)$_2$ZrCl$_2$ structure pyrrolyl is provided in the experimental, compound XIV, (C$_{20}$H$_{16}$N)$_2$ZrCl$_2$ bis-([a,i] dibenzo-3,4,5,6-tetrahydrocarbazolyl) zirconium dichloride, structure phospholyl provided in the experimental, compound XVIII, (C$_{22}$H$_{20}$N)$_2$ZrCl$_2$ bis-([a,i]di(methylbenzo)-3,4,5,6-tetrahydrocarbazolyl) zirconium dichloride, (C$_{20}$H$_{16}$N) (C$_5$H$_5$)ZrCl$_2$ ([a,i]dibenzo-3,4,5,6-tetrahydrocarbazolyl) cyclopentadienyl zirconium dichloride, structure phospholyl provided in the experimental, compound XVIII, 1,2-C$_2$H$_4$(3-PC$_8$H$_5$)$_2$ZrCl$_2$ (1,2-ethylene-bis(3-phosphindolyl) zirconium dichloride, Me$_2$Si(3-PC$_8$H$_5$)$_2$ZrCl$_2$ (dimethylsilylbis-(3-phosphindolyl) zirconium dichloride, 1,2-C$_2$H$_4$(3-PC$_8$H$_9$)$_2$ZrCl$_2$ (1,2-ethylene-bis(tetrahydro-3-phosphindolyl) zirconium dichloride, Me$_2$Si(3-PC$_8$H$_9$)$_2$ZrCl$_2$ (dimethylsilylbis-(tetrahydro-3-phosphindolyl) zirconium dichloride, 1,2-C$_2$H$_4$([benz]3-PC$_8$H$_5$)$_2$ZrCl$_2$ (1,2-ethylene-bis([benz]3-phosphindolyl) zirconium dichloride, Me$_2$Si([benz]3-PC$_8$H$_5$)$_2$ZrCl$_2$ dimethylsilylbis-([benz]3-phosphindolyl) zirconium dichloride, (2-Ph-3,4-Me$_2$-5-(SiMe$_2$N-t-Bu)C$_4$P) ZrCl$_2$ 2-phenyl-3,4-dimethyl-5-(dimethylsilyl-tertiarybutylamide)phospholyl zirconium dichloride, (2-Ph-3,4-Me$_2$-5-(SiMe$_2$N-t-Bu)C$_4$P)ZrMe$_2$ 2-phenyl-3,4-dimethyl-5-(dimethylsilyl-tertiarybutylamide)phospholyl zirconium dimethyl (C$_{18}$H$_{19}$P)$_2$ZrCl$_2$ bis-(1-butyl-2-phenyl-3-phosphindolyl) zirconium dichloride.

The present invention further concerns a catalyst composition for the oligomerization or polymerization of olefinically unsaturated hydrocarbons, comprising a first component which is an organometal complex as defined above and a second component which acts as a co-catalyst.

The second component can be an aluminoxane, in particular methyl aluminoxane. Aluminoxanes are well known polymeric aluminum compounds, which can be represented by the general formulae (R-Al-O) which represents a cyclic compound, and R(R-Al-O)-AlR$_2$, which represents a linear compound. In these general formulae R is an alkyl, preferably of 1–5 carbon atoms and n is 1–100, especially 5–20. The best known aluminoxane is methyl aluminoxane (MAO). Also effective is a mixture of methyl aluminoxane and isobutyl aluminoxane (IBAO). The aluminoxanes are suitably prepared by reacting water with trialkylaluminum compounds, whereby usually a mixture of the linear and cyclic polymer is obtained.

Preferred organometal complexes according to the invention for combination with aluminoxanes contain at least two groups Q, being the same or different and chosen from hydrogen, alkyl, aryl, alkenyl, alkylaryl, arylalkyl or cyclopentadienyl, any of which having from 1 to 20 carbon atoms and optionally being further substituted, or halide.

The molar ratio of the aluminoxane to the organometal complex according to the invention may vary between wide ranges. Suitably the molar ratio is within the range of from 2 to 10000, preferably from 50 to 2000, calculated as gram atoms of aluminum per gram atom of metal M.

The catalyst composition of the organometal complex of the present invention with the aluminoxane may be prepared prior to the contacting with the olefinically unsaturated compounds to be polymerized, or they may be prepared in situ i.e. in the presence of the feed. It is preferred to prepare these catalyst compositions by mixing together the two components in solution in a solvent such as toluene to form a liquid catalyst system.

Alternatively, the two components of the catalyst composition according to the invention can be the cation and anion of an ionic compound of the general formula

wherein the components of the cation are as defined hereinbefore with the proviso that q is at least 1 and at least one Q is chosen from the group of hydrogen, aryl, alkyl, alkenyl, alkylaryl, arylalkyl or cyclodienyl, any of which having from 1 to 20 carbon atoms and optionally being further substituted and n+the sum of the valencies of the Q groups +1 equals the valency of the metal −1, and the anion [An−] is bulky and substantially non-coordinating under the reaction conditions.

It will be appreciated that when the two components of the catalyst composition are the cation and anion of an ionic compound as broadly defined hereinbefore, this ionic compound can be produced in different ways.

One way to produce the ionic catalytic compound is by reacting an organometal complex as defined hereinbefore with a compound of a bulky and substantially non-coordinating anion. The cation associated with the bulky anion should be capable of abstracting an anion from the heterocyclopentadienyl organometal complex to form a heterocyclopentadienyl ionic compound, rendering itself neutral. An illustrative example for such reactions is:

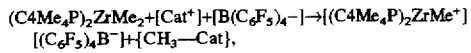

whereby, when the cation [Cat+] is for example [PhNH(CH3)2+], {CH3—Cat} will become CH4+PhN(CH3)2, and when the cation is [Ph3C+] {CH3—Cat} will become Ph3C—CH3.

Preferably, the bulky and substantially non-coordinating anion is a carborane anion, suitably a carborane anion of the formula

[B11CH12—]. Such carboranes are known and can be prepared by methods such as that of K. Shelly et al (J. Am. Chem. Soc. 107 1985 5955). Other preferred bulky boron containing anions are of the general formula [BR4−], wherein R is C6H5, C6F5, 3,5-((CF3)2C6H3) and 4-FC6H4, such as the tetra(perfluorophenyl)boron anion.

The cation is suitably a proton-donating cation, preferably a quaternary ammonium cation such as a trialkylammonium cation, for example tri-n-butylammonium cation. Alternatively, a cation may be used which is not proton-donating, such as a metal cation e.g. a silver ion, or a triphenylcarbenium ion.

The catalyst composition may be formed by mixing together the organometallic complex and the compound of the bulky and substantially non-coordinating anion, preferably in solution in a suitable non-polar solvent such as toluene, chlorobenzene, an alkane or an alkene, to form a liquid catalyst system. The two components are generally employed in substantially equimolar amounts, although the molar ratio of the first component to the second component may vary within the range of from 0.1 to 5.0. Such a quantity of the catalyst system is usually employed in the reaction mixture as to contain from $10^{-1}$ to $10^{-7}$ gram atoms, in particular from $10^{-3}$ to $10^{-5}$ gram atoms, of the metal per mole of olefinically unsaturated hydrocarbon to be reacted.

Another way to produce the ionic catalyst is by reacting a suitable heterocyclopentadienyl organometallic compound with a neutral, strongly Lewis acidic compound which is capable of abstracting one of the radicals Q of the organometallic compound, thereby also contributing a bulky and substantially non-coordinating anion to the completed catalyst compound. An illustrative example of such a reaction, related to the procedure described by X. Yang et al., J. Am. Chem. Soc. 113 1991 3623, is:

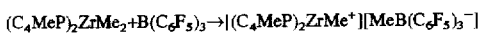

Although not required for catalytic activity, further components may be added to the catalytic composition according to the invention, for example in order to increase the solubility or the lifetime of the composition. For the ionic catalytic compositions, alkylaluminoxanes in relatively small amounts are efficient solubilizing and scavenging agents.

The complete catalyst compositions according to the invention can be used in solution. Alternatively, the catalyst composition can be loaded on a solid carrier.

Many inert materials are suitable in principle for use as carrier materials. Examples are magnesium chloride and the oxides of silicon, aluminum, magnesium, titanium, zirconium and iron and amorph and crystalline mixtures thereof, in particular silica, alumina, silica-alumina and zeolites. The carrier materials are used in the form of particles, suitably smaller than 1 mm and having a specific surface area greater than 1 m2/g.

Very suitable in as carriers for the catalysts of this invention are the materials, composed of aluminoxane and silica, such as are marketed by WITCO GmbH, Bergkamen, Germany. Both neutral and ionic catalytic compositions as defined hereinbefore, containing the heterocyclopentadienyl organometallic complexes according to the invention, can be combined with these materials to form solid catalytically active compositions.

A further aspect of the present invention is the process of oligomerization or polymerization of one or more olefinically unsaturated hydrocarbon(s) in the presence of catalyst compositions as defined hereinbefore. The term oligomerization is intended to define an unbranched or branched chain product, built up from 2 to about 20 monomeric olefin elements.

The oligomerization or polymerization reaction according to the invention can be carried out in the liquid phase. When the catalyst compositions are loaded on an inert carrier the reaction is heterogeneous and can also be carried out in the gas phase. The reaction can be carried out in batch or in continuous operation.

The oligomerization or polymerization reaction is generally, although not necessarily, carried out in an inert liquid which is suitably also the solvent for the catalyst components. The reaction is suitably carried out at an elevated temperature, preferably in the range of from 20° to 175° C., more preferably at 50° to 150° C. The reaction is suitably carried out under conditions of moderately elevated pressure, preferably in the range of from 100 to 10000 kPa, more preferably from 500 to 6000 kPa. The conditions of temperature and pressure can be varied within these ranges in order to maximize the yield of the desired product, as can be readily established by those skilled in the art.

The starting reactants may be supplied to the reactor together with an inert diluent, such as nitrogen or helium when the reactant is gaseous, and a liquid solvent, e.g. the same solvent as that of the catalyst components, when the reactant is in the liquid form.

The reaction is preferably carried out in the absence of air or moisture.

Reaction times of from 1 minute to 5 hours have been found to be suitable, depending on the activity of the catalyst system and on the reaction conditions. When the reaction is homogeneous it can be terminated by adding to the reaction mixture a conventional catalyst deactivating agent (proton donor) such as water, methanol, or another alcohol. Alternatively, the reaction can simply be terminated by the introduction of air.

The products of the reaction are typically mixtures. They may be suitably recovered by separation techniques known in the art. If desired, unconverted starting material and products having a molecular weight outside the desired molecular weight may be recovered, processed if necessary and recycled to be used as starting material in a subsequent oligomerization reaction.

The present invention has an outstanding versatility and the products may vary very widely in their molecular weight which may be from that of dimers of the starting olefins to polymers of over 1000000 daltons, and in their molecular composition. The catalysts of the present invention were found to be particularly advantageous in the production of (co)oligomers and of (co)polymers having a relatively low molecular weight, i.e. below about 50000 daltons, for the production of which prior art catalysts have been found to be less suitable.

The properties of the products may be controlled by a proper choice of the catalyst composition, the starting material(s) and the reaction conditions. Also, when the presence of an unsaturated end group in the product is not a requirement, the molecular weight thereof can be controlled by adding hydrogen to the reaction mixture.

Catalysts according to the present invention are particularly suitable for the production of oligomers of the feed olefins. Oligomeric products which are of particular interest are linear alpha alkenes having a chain length within the range of 5 to 24 carbon atoms, of which those having between 6 and 10 carbon atoms in the chain are currently more particularly preferred. They are in great demand as intermediates for the preparation of detergents, lubricant additives and polyolefins.

Catalysts according to the present invention are also particularly suitable for the production of liquid atactic polymers, of which those having an olefinically unsaturated end group, more preferably a vinylidene end group, and a number average molecular weight of from 300 to 10000 daltons are of particular current interest. Such liquid atactic vinylidene polymers, in particular those which are prepared from propylene, are useful as intermediates, e.g. for the preparation of dispersants for lubricating oil compositions.

Catalysts of the present invention are further suitable for the production of solid polymers, such as polyethylenes and copolymers thereof, polypropylenes and copolymers thereof, highly branched polypropylenes, and polystyrenes and copolymers thereof.

Mono- and bis- heterocyclopentadienyl-based catalysts of the present invention having a bulky substituent as defined hereinbefore on one or both of the 2 and 5 positions on the ring, for examples both of the complexes bis(2,5-diphenylphospholyl) zirconium dichloride and (2,5-diphenylphospholyl)(cyclopentadienyl) zirconium dichloride were found to be particularly effective in the polymerization and copolymerization of olefins other than ethene alone, such as propene and octene with ethene.

A class of products which is presently of particular interest are the syndiotactic polystyrenes. Catalysts according to the present invention, in particular monophospholyl metal complexes, e.g. substituted phospholyl titanium trichloride catalysts with MAO cocatalyst, were found to selectively catalyze the polymerization of styrene to syndiotactic polystyrene.

The invention will be further illustrated by the following Examples.

EXAMPLE A

Syntheses of heterocyclopentadienyl Group IV complexes.

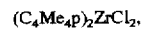  I

A solution of 1-phenyl-2,3,4,5-tetramethylphosphole, 2.87 g (13.3 mMol) in 50 ml of tetrahydrofuran was treated with lithium foil (3–4 molar equivalent) for 2–3 h. The excess of lithium was removed and the reaction mixture was cooled to 0° C. To the cooled solution 0.59 g of $AlCl_3$ was added. After 30 minutes at 0° C. the resulting mixture was slowly added to a stirred suspension of $ZrCl_4$, 1.55 g (6.6 mMol) in 20 ml toluene at 0° C. After 30 minutes the reaction mixture was evaporated to dryness and the residue taken up in hexane and evaporated to dryness. The resulting material was chromatographied over $SiO_2$ with hexane as eluent. Evaporation of the volatiles from the eluted hexane fraction afforded 2.0 g I, which was characterized by $^1H-$, $^{13}C-$, and $^{31}P-NMR$.

(Literature: F. Nief, F. Mathey, L. Ricard Organometallics 7, 1988, 921–926).

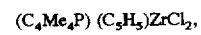  II

Complex II was prepared by a similar procedure as described for reaction of I, except that $ZrCl_4$ was replaced with $C_5H_5ZrCl_3$. $^1H$-NMR and $^{13}C$-NMR of the isolated product were in agreement with its formulation as $(C_4Me_4P)$ $(C_5H_5)ZrCl_2$. Yield ca. 60%.

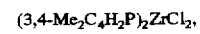  III

Complex III, was prepared according to the route described for I except that the phospholyl anion in this case was $(3,4-Me_2C_4H_2P)^-$.

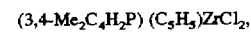  IV

Complex IV was prepared according to the route described for II except that the phospholyl anion in this case was $(3,4-Me_2C_4H_2)^-$.

  V

A mixture of $(C_4Me_4P)_2ZrCl_2$ (1.75 mMol) and (norbornyldiene)W(CO)$_4$ (1.80 mMol) in methylcyclohexane was kept at 75° C. for 5 hours, then cooled to room temperature. The solids were filtered off and the filtrate was evaporated to yield a red solid. Yield 50%. (Literature: Nief, F. Mathey, F., Ricard, L. J. Organomet. Chem. 1990, 384, 271).

  VI 1.0 g of 2.5-Ph$_2$C$_4$H$_2$PPh was dissolved in tetrahydrofuran and reacted with 0.09 g of lithium. After 45 minutes excess lithium was removed and the resulting solution chilled to 0° C. To the cold solution 0.145 g of AlCl$_3$ was added and the reaction mixture was stirred at 0° C. for about 30 minutes. To the resulting reaction mixture 0.35 g of ZrCl$_4$ was added and stirring was continued for another 30 minutes at room temperature. After that period the reaction mixture was checked on the presence of phospholyl anion by means of $^{31}$P-NMR. When all phospholyl anion had reacted solvent was removed under vacuo. The resulting solids were treated with dichloromethane and subsequently the insoluble fraction was rapidly removed by centrifugation and decanting the mother liquor. The obtained dichloromethane solution was immediately evaporated and the product treated with toluene. In this process an oily phase is formed together with an clear solution. This clear solution was separated and subsequently all volatiles evaporated of. The residue was taken up in diethyl ether and the suspension stirred until all oil had solidified. The precipitate was suspended in toluene, the solids were removed by centrifugation and decanting the mother liquor, and the resulting solutions concentrated and subsequently cooled to −25° C. After 48 hours crystals had formed which were isolated. The product was characterized by $^1$H-NMR, $^{13}$C-NMR, and $^{31}$P-NMR. The data are in agreement with its formulation as (2,5-Ph$_2$C$_4$H$_2$P)$_2$ZrCl$_2$.

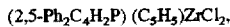

(2,5-Ph$_2$C$_4$H$_2$P) (C$_5$H$_5$)ZrCl$_2$,   VII

Similarly to the preparation of (2,5-Ph$_2$C$_4$H$_2$P)$_2$ZrCl$_2$, VI, a solution was prepared of the (2,5-Ph$_2$C$_4$H$_2$P) anion in tetrahydrofuran and subsequently reacted with AlCl$_3$. This reaction mixture was dropwise added to a solution of (C$_5$H$_5$)ZrCl$_3$ in tetrahydrofuran at room temperature and the whole mixture stirred for another 30 minutes. Subsequently, the reaction products were worked up as described for the VI complex with dichloromethane, ether, and toluene. After the latter step the volatiles were removed and the residue thoroughly washed with hexane. After decanting the hexane layer and drying under vacuo a solid was isolated.

$^1$H-NMR, $^{13}$C-NMR, and $^{31}$P-NMR of the solid are in agreement with its formulation as (2,5-Ph$_2$C$_4$H$_2$P) (C$_5$H$_5$) ZrCl$_2$.

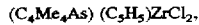

(C$_4$Me$_4$As) (C$_5$H$_5$)ZrCl$_2$,   VIII

1-Phenyl-2,3,4,5-tetramethylarsole (1.18 g, 4.5 mMol) was reacted with excess lithium metal in tetrahydrofuran at room temperature. After two hours the reaction mixture was cooled to −78° C. and transferred by canula onto solid anhydrous AlCl$_3$ (0.2 g, 1.5 mMol). The reaction mixture was allowed to warm to room temperature while it was continuously stirred. The resulting solution was transferred by canula to a stirred tetrahydrofuran suspension of (C$_5$H$_5$)ZrCl$_3$ (1.2 g, 4.5 mMol) at −78° C. The reaction mixture was slowly warmed to room temperature and stirred for another 16 hours. Subsequently, the solvent was stripped in vacuo to afford a residue which was extracted with 50 ml of hexane. Hereafter, the residue was extracted with toluene. After evaporation of the volatiles from the toluene solution a powder remained which was characterized as (C$_4$Me$_4$As) (C$_5$H$_5$) ZrCl$_2$ with a small amount of a product resulting from reaction of phenyl-lithium with tetrahydrofuran.

(2,5-Ph$_2$-3MeC$_4$HP)$_2$ZrCl$_2$,   IX 0.64 g of 1,2,5-Ph$_3$-3-MeC$_4$HP was stirred with excess of lithium foil in 40 ml of THF at room temperature. After stirring for 45 minutes the excess lithium was removed and 0.5 ml of t-butylchloride was added to the reaction mixture. The mixture was warmed to 55° C. and stirring was continued for 30 minutes. The solvents were evaporated to yield the crude phospholyl lithium compound. To the crude lithium compound was added 30 ml of diethylether and the mixture was cooled to −78° C. Subsequently a suspension of 228 mg of ZrCl$_4$ in toluene was slowly added and the mixture was allowed to warm to room temperature. Hereafter the solvents were evaporated and the remainder dissolved in diethylether and chromatographied over silica. The solvents were evaporated and the resulting material washed with hexane. After drying under vacuum the solids were isolated. The product was characterized by $^1$H-NMR, $^{13}$C-NMR, and $^{31}$P-NMR. The data are in agreement with its formulation as (2,5-Ph$_2$-3-MeC$_4$HP)$_2$ZrCl$_2$.

(2,5-Ph$_2$-3,4-Me$_2$C$_4$P)$_2$ZrCl$_2$,   X 0.59 g of 1,2,5-Ph$_3$-3,4-Me$_2$C$_4$P was stirred with excess of lithium foil in 30 ml of thf for 4 hours at room temperature. Hereafter, excess lithium foil was removed and 0.6 ml of t-BuCl was added. The mixture was warmed to 55° C. and stirred for 45 minutes. Subsequently, the solution was cooled to room temperature and a suspension of 200 mg of ZrCl$_4$ in toluene added dropwise. After addition of ZrCl$_4$ was complete, the reaction mixture was warmed to 60° C. for 30 minutes. After this period the volatiles were removed under vacuum and the solids extracted with toluene. Upon evaporation of the toluene a solid was obtained which was recrystallized from CH$_2$Cl$_2$. The product was characterized by $^1$H-NMR, $^{13}$C-NMR, and $^{31}$P-NMR. The data are in agreement with its formulation as (2,5-Ph$_2$-3,4-Me$_2$C$_4$P)$_2$ZrCl$_2$.

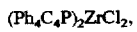

(Ph$_4$C$_4$P)$_2$ZrCl$_2$,   XI 1.5 g of 1,2,3,4,5-Ph$_5$C$_4$P was stirred with excess of lithium foil in thf at room temperature for 16 hours. Hereafter, the excess lithium was removed, 2 ml t-BuCl was added, the reaction mixture was warmed to 55° C. for one hour and subsequently all volatiles were removed under vacuo. The remaining solids were washed twice with hexane, dried under vacuo, and isolated. 0.5 g of the isolated product was suspended in 40 ml of diethylether and added to a suspension of 130 mg of ZrCl$_4$ in 10 ml of toluene at 0° C. After stirring the reaction mixture at room temperature for 45 minutes, the temperature of the reaction mixture was raised to 45° C. and stirring was continues for 30 minutes. The precipitate was removed by centrifugation and, subsequently, the volatiles under vacuum. The resulting solid was washed with hexane, isolated, and characterized by $^1$H-NMR, $^{13}$C-NMR, and $^{31}$P-NMR. The spectral data are in agreement with its formulation as (Ph$_4$C$_4$P)$_2$ZrCl$_2$.

(2-Me-5-PhC$_4$H$_2$P)$_2$ZrCl$_2$,   XII 0.41 g of 1,2-Ph$_2$-5-MeC$_4$H$_2$P was dissolved in thf and reacted with an excess of lithium foil. When conversion of the starting material into the corresponding anion was complete (as measured by $^{31}$P-NMR), the excess lithium was removed and 115 mg of AlCl$_3$ was added at 0° C. The resulting reaction mixture was stirred for 30 minutes and subsequently, slowly added to 190 mg of ZrCl$_4$ in thf at 0° C. After stirring the solution for 60 minutes at room temperature, the volatiles were evaporated off and the solvents extracted with toluene. Evaporation of the toluene, extraction of the obtained solids with CH$_2$Cl$_2$, removal of the volatiles under vacuum, and subsequent washing of the solids with hexane afforded a precipitate which was isolated and characterized by $^1$H-NMR, $^{13}$C-NMR, and $^{31}$P-NMR. The spectral data are in agreement with its formulation as (2-Me-5-PhC$_4$H$_2$P)$_2$ZrCl$_2$ (2 isomers).

(2-(3,5-t-Bu$_2$-4-OMeC$_6$H$_2$)-5-MeC$_4$H$_2$P)$_2$ZrCl$_2$,     XIII 2.34 g of 1-Ph-2-(3,5-t-Bu$_2$-4-OMeC$_6$H$_2$)-5-MeC$_4$H$_2$P was dissolved in 100 ml of thf and reacted with excess sodium for 16 hours at room temperature. After removal of excess sodium, 2 ml of t-butylchloride was added to the reaction mixture, the temperature was raised to 55° C., and stirring continued for 2 hours. Subsequently the solvent was evaporated and the resulting product stirred with 40 ml of hexane until a suspension was obtained. Hereafter the suspension was centrifugated, the solution decanted, the solid product washed with 25 ml of hexane, dried under vacuum and isolated. 1.4 g of the isolated product was suspended in 25 ml of toluene and added to 450 mg of ZrCl$_4$ suspended in 10 ml of toluene in 45 minutes and the resulting mixture was stirred for 16 hours. The resulting reaction mixture was centrifugated, the supernatant decanted, and the solid remainder washed twice with 10 ml of toluene. The toluene supernatant and washings were combined and the solvent was evaporated. Subsequently the resulting product was dissolved in 50 ml of hexane, centrifugated and concentrated to about 15 ml. Upon cooling crystals were formed which were isolated after drying under vacuum. The product was characterized by $^1$H-NMR, $^{13}$C-NMR, and $^{31}$P-NMR. The data are in agreement with its formulation as (2-(3,5-t-Bu$_2$-4-OMeC$_6$H$_2$)-5-MeC$_4$H$_2$P)$_2$ZrCl$_2$.

(C$_{17}$H$_{12}$P)$_2$ZrCl$_2$,     XIV

Phosphole Ph-PC$_{17}$H$_{12}$ was dissolved in thf and treated with sodium. After stirring for 1.5 hours the excess of sodium was removed and 1 ml of t-butylchloride was added. The mixture was warmed to 52° C. and stirring continued for 1 hour. The solvents were evaporated and the remainder washed twice with hexane/toluene (9:1). After drying under vacuum the solids were isolated. A suspension of 267 mg of this solid in 15 ml of toluene was added to a suspension of 0.33 mMol of ZrCl$_4$ in 10 ml of toluene at room temperature. After stirring overnight the mixture was centrifugated, the clear orange solution decanted and the solvents evaporated. The remaining solids were washed twice with hexane and subsequently treated with a 0.5 ml of dichloromethane. The resulting solids were isolated and extracted with benzene and dichloromethane. After evaporation of the solvents a precipitate was isolated. The product was characterized by $^1$H-NMR, $^{13}$C-NMR, and $^{31}$P-NMR. The data are in agreement with its formulation as (C$_{17}$H$_{12}$P)$_2$ZrCl$_2$.

(2,5-n-Pr$_2$C$_4$H$_2$P)$_2$ZrCl$_2$,     XV

Compound XV was prepared in the same way as compound I by replacing Me$_4$C$_4$PPh with 2,5-n-Pr$_2$C$_4$H$_2$PPh. The NMR data of the isolated product are in agreement with its formulation as XV.

(2,5-t-Bu$_2$C$_4$H$_2$P) (C$_5$H$_5$)ZrCl$_2$,     XVI

A suspension was made of 220 mg phospholyl anion (0.63 mMol) in toluene and was cooled to −40° C. To this suspension was added 83 mg (C$_5$H$_5$)ZrCl$_3$ as a solid. The reaction was stirred for 20 hours at room temperature. The formed LiCl was filtered off. An equal amount of hexane was added to the toluene and stored at −40° C. for two days. The yellow crystalline powder which had formed was isolated after decanting the mother liquor and drying under vacuum. The product was characterized by $^1$H-NMR, $^{13}$C-NMR, and $^{31}$P-NMR. The data are in agreement with its formulation as (2,5-t-Bu$_2$C$_4$H$_2$P) (C$_5$H$_5$)ZrCl$_2$.

(2,5-c-Pe$_2$C$_4$H$_2$P)$_2$ZrCl$_2$,     XVII

1-Ph-2,5-c-Pe$_2$C$_4$H$_2$P was dissolved in thf and reacted with excess Na at room temperature. When all starting phosphole was converted into the anion, excess Na was removed and t-BuCl was added and the reaction mixture warmed to 55° C. Subsequently, the solvent was removed and the remaining solids washed with hexane and dried under vacuum. The so-obtained product was reacted with a suspension of ZrCl$_4$ in toluene at room temperature. After reaction, the solids were removed by centrifugation, the toluene solution concentrated, some hexane added, and cooled to −20° C. Upon cooling yellow crystalline material formed which was isolated after decantation of the mother liquor and drying under vacuum. The product was characterized by $^1$H-NMR, $^{13}$C-NMR, and $^{31}$P-NMR. The data are in agreement with its formulation as (2,5-c-Pe$_2$C$_4$H$_2$P)$_2$ZrCl$_2$.

(2,5-i-Pr$_2$C$_4$H$_2$P)$_2$ZrCl$_2$,     XVIIA 309 mg phospholyl anion (1.72 mMol) was added to a 15 ml toluene and cooled to −40° C. 114 mg ZrCl$_4$ was added and the suspension was stirred for 20 hours at room temperature. The precipitate which had formed was removed and to the toluene layer an equal amount of hexane was added. Upon cooling of this solution to −40° C. a yellow compound crystallized. After removing the mother liquor and drying the solid under vacuum, it was isolated. NMR data are in agreement with formulation of the material as (2,5-i-Pr$_2$C$_4$H$_2$P)$_2$ZrCl$_2$.

(C$_{20}$H$_{16}$N) (C$_5$H$_5$)ZrCl$_2$,     XVIII

Dibenzo [a,i]-3,4,5,6-tetrahydrocarbazolyl-lithium, C$_{20}$H$_{16}$NLi, 100 mg, was added to a suspension of 95 mg of C$_5$H$_5$ZrCl$_3$ in toluene at room temperature. After stirring for 3 hours the precipitate is removed and the solution concentrated and cooled to −20° C. After 16 hours the resulting crystals were isolated and dried under vacuum. $^1$H-NMR and $^{13}$C-NMR data of the crystalline material are in agreement with its formulation as (C$_{20}$H$_{16}$N) (C$_5$H$_5$)ZrCl$_2$.

(C$_{20}$H$_{16}$N)$_2$ZrCl$_2$,     XIX

Dibenzo [a,i]-3,4,5,6-tetrahydrocarbazolyl-lithium, C$_{20}$H$_{16}$NLi, 100 mg, was added to a suspension of 42 mg of ZrCl$_4$ in toluene at room temperature. After stirring for 3 hours the precipitate is removed and the solution concentrated and cooled to −20° C. After 16 hours the resulting crystals were isolated and dried under vacuum. $^1$H-NMR and $^{13}$C-NMR data as well as elemental analyses of the crystalline material are in agreement with its formulation as (C$_{20}$H$_{16}$N)$_2$ZrCl$_2$.

3,4-Dimethylphospholyl titanium trichloride,     XX

To a solution of 50 mg bis(3,4-dimethylpholyl) zirconium dichloride in 1 ml of C$_6$D$_6$ was added 0.5 ml 1 M TiCl$_4$ in toluene at room temperature. The solution turned bright red and a precipitate formed. The solvents were evaporated of and the remainder extracted with hexane. The crystals which formed while cooling to −40° C. were separated, dried, and characterized by NMR.

NMR data of (3,4-Me$_2$C$_4$H$_2$P)TiCl$_3$ (CD$_2$Cl$_2$, δ, ppm): $^{31}$P:190.07. $^1$H: 1.81(s,3), 6.78(d,1J$_{P-H}$=35.5 Hz).

2,3,4,5-Tetramethylphospholyl titanium trichloride,  XXI

To a solution of 307 mg of bis-(2,3,4,5-tetramethylphospholyl)-zirconium dichloride in 40 ml of hexane was added 1.5 ml 1M solution of TiCl$_4$ in toluene at −78° C. The yellow-orange solutions darkened immediately and was allowed to warm to room temperature. Subsequently the solvents were evaporated and the product extracted with hexane. After evaporation of the solvent the remaining solids were collected and characterized by NMR.

NMR data of (2,3,4,5-Me$_4$C$_4$P)TiCl$_3$ (CD$_2$Cl$_2$, δ, ppm): $^{31}$P:212.06. $^1$H: 2.47(s,3), 2.68(d,3,J$_{P-H}$=9.5 Hz).

2,5-Diphenylphospholyl titanium trichloride,  XXII

To a solution of 502 mg of 1,2,5-triphenylphosphole in 30 ml of tetrahydrofuran was added an excess of lithium foil at room temperature. After stirring for one hour the excess of lithium was removed and the solution was cooled to 0° C. To the chilled solution 0.33 equivalent of AlCl$_3$ was added and stirring was continued for another 30 minutes. Subsequently the solution was cooled to −20° C. and 0.5 ml of trimethyl chloro silane was added. After warming the reaction mixture to room temperature the volatiles were evaporated of and the remaining residue characterized. $^{31}$P-NMR showed that 87% of the residue consisted of 2,5-diphenyl-trimethylsilyl phosphole ($^{31}$P-NMR (CD$_2$Cl$_2$): −38.53 ppm, $^1$H-NMR (CD$_2$Cl$_2$) −0.24(d,9), 7.2–7.6(m,12). This residue was taken up in 30 ml of hexane and 2.5 ml of 1.0M TiCl$_4$ in toluene was added at −78° C. The reaction mixture was allowed to warm to room temperature and the solvents were evaporated. The product was obtained by extraction of the residue with dichloromethane and recrystallization of the obtained solids from the same solvent.

NMR data of (2,5-Ph$_2$C$_4$H$_2$P)TiCl$_3$ (CD$_2$Cl$_2$, δ, ppm): $^{31}$P:160.79. $^1$H: 7.50–7.52(m,6), 7.90–7.93(m,4), 8.09–8.10 (d,2).

2,3,4,5-Tetraphenylphospholyl titanium trichloride,  XXIII

To a solution of 100 mg of pentaphenylphosphole in 25 ml of THF was added an excess of lithium foil. After stirring at room temperature for 3 hours the excess of lithium was removed, excess of trimethylsilyl chloride was added, and the reaction mixture stirred for another 15 minutes. Hereafter the volatiles were removed under vacuum and the remainder extracted with dichloromethane. Evaporation of the solvent afforded trimethylsilyl 2,3,4,5-tetraphenyl phosphole ($^{31}$P-NMR: −23.93 ppm; $^1$H-NMR: −0.25(d,9), 7.0–7.4(m,20)ppm) plus some impurities. This product was taken up in hexane and 1 ml of 1.0M solution of TiCl$_4$ in toluene was added at −78° C. The mixture was allowed to warm to room temperature and the solvents were evaporated of. After extraction of the residue with dichloromethane and recrystallization of the obtained product from dichloromethane/hexane the desired compound was isolated as dark-purple crystals.

NMR data of (2,3,4,5-Ph$_4$C$_4$P)TiCl$_3$ (CD$_2$Cl$_2$, δ, ppm): $^{31}$P:189.93. $^1$H: 7.20–7.50(m).

2,5-Diphenyl-3,4-dimethylphospholyl titaniumtrichloride,  XXIV 2,5-Diphenyl-3,4-dimethylphospholyl titaniumtrichloride was synthesized by the reaction of TiCl$_4$ with bis-(2,5-diphenyl-3,4-dimethylphospholyl)zirconium dichloride in hexane/toluene at room temperature in a way essentially similar to the synthesis of XXI.

NMR data of (2,5-diphenyl-3,4-dimethylphospholyl) titaniumtrichloride (CD$_2$Cl$_2$, δ ppm): $^{31}$P: 182.15 $^1$H: 2.70 (s,6), 7.4–7.7 (m,10).

2,5-Di-t-butylphospholyl titanium trichloride,  XXV 2,5-Di-t-butylphospholyl titanium trichloride was synthesized in a way essentially similar to XXIII, except that 1-phenyl-2,5-di-t-butylphosphole was used as the starting material.

(C$_4$Me$_4$P)$_2$ZrMe$_2$,  XXVI (C$_4$Me$_4$P)$_2$ZrCl$_2$, I, was dissolved in toluene and reacted with 2 equivalents of MeLi dissolved in diethyl ether at −70° C. During addition of the MeLi the reaction mixture changed from orange via green to yellow and a precipitate had formed. After one hour the reaction mixture was centrifugated and the solids removed by decanting the mother liquor. After evaporation of the toluene, the resulting solid was extracted with hexane. Concentration of the hexane layer and subsequent cooling afforded yellow crystalline (C$_4$Me$_4$P)$_2$ZrMe$_2$. Yield ca. 60%.

(C$_4$Me$_4$P) (C$_5$H$_5$)ZrMe$_2$,  XXVII

Complex XXVII was prepared similar to compound XXVI except that (C$_4$Me$_4$P) (C$_5$H$_5$)ZrCl$_2$, II, was used instead of I.

(C$_5$Me$_5$) (2,5-Me$_2$C$_4$H$_2$N)ZrCl$_2$,  XXVIII 1.76 g (5.3 mMol) of (C$_5$Me$_5$)ZrCl$_3$ and 0.53 g (5.3 mMol) of Li(2,5-(Me$_2$C$_4$H$_2$N) were weighted into a Schlenkvessel. The flask was cooled to −196° C., 50 ml of toluene was added and the contents was slowly warmed up to room temperature. After the mixture had been stirred for 18 hours at room temperature, a pale yellow suspension had formed. The precipitate was allowed to settle and the clear yellow solution was filtered. Concentration of the filtrate and cooling to −20° C. produced pale-yellow needles. Isolation afforded the title compound in 35% yield.

(C$_5$Me$_5$) (2,5-t-Bu$_2$C$_4$H$_2$N)ZrCl$_2$,  XXIX

A similar procedure as described for (C$_5$Me$_5$) (2,5-Me$_2$C$_4$H$_2$N)ZrCl$_2$, XXVIII, was applied. The reaction time was 27 h at room temperature. Yield 21%.

(C$_5$Me$_5$) (2,5-Me$_2$C$_4$H$_2$N) ZrMe$_2$,  XXX 1.8 ml of a 1.6M solution of MeLi in diethyl ether was slowly added to a stirred solution of 0.51 g (1.29 mMol) of (C$_5$Me$_5$) (2,5-Me$_2$C$_4$H$_2$N)ZrCl$_2$, XXVIII in 40 ml of diethyl ether. The solution was stirred for 4 h at room temperature. The solvent was removed in vacuo and the residue was extracted with pentane. The pale-yellow pentane solution was concentrated and cooled to −30° C. The yellow microcrystals were isolated. Yield 0.21 g (66%). 31P-NMR.

(C$_4$Me$_4$P) (C$_5$Me$_5$)ZrCl$_2$,  XXXI

Complex XXXI was prepared by a similar procedure as described for II except that (C$_5$H$_5$)ZrCl$_3$ was replaced with (C$_5$Me$_5$) ZrCl$_3$.

(C$_4$Me$_4$P) (C$_5$Me$_5$)ZrMe$_2$,  XXXII

Complex XXXII was prepared by a similar procedure as described for XXVII except that XXXI was used instead of II.

(C$_5$Me$_5$) (2,5-t-Bu$_2$C$_4$H$_2$N) ZrMe$_2$,  XXXIII

A similar procedure as given (C$_5$Me$_5$) (2,5-Me$_2$C$_4$H$_2$N) ZrMe$_2$, XXX, was applied except that (C$_5$Me$_5$) (2,5-t-

$Bu_2C_4H_2N)ZrCl_2$. XXIX, was used as the starting material. The title compound was isolated as pale-orange crystals in 29% yield. The NMR data of the orange material are in line with its formulation as $(C_5Me_5)$ $(2,5-t-Bu_2C_4H_2N)$ $ZrMe_2$.

EXAMPLE B

Syntheses of ionic catalyst compositions

XXXIV $(C_4Me_4P)_2ZrMe_2$, XXVI, (50 mg, 0.125 mMol) was dissolved in toluene and reacted with $[Bu_3NH^+][B_{11}CH_{12}^-]$ (41.5 mg, 0.125 Mol) at room temperature. An orange-brown precipitate formed which was isolated by centrifugation of the reaction mixture and decanting of the mother liquor. The obtained precipitate was washed once more with fresh toluene and thereafter dried under vacuum. The resulting material was used as a catalyst in olefin polymerizations. It is moderately well soluble in bromobenzene and its $^1$H-NMR in $d^5$-bromobenzene shows only traces of free $Bu_3N$.

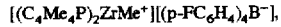
XXXV $(C_4Me_4P)_2ZrMe_2$, XXVI (50 mg, 0.125 mMol) was dissolved in toluene and reacted with $[PhNMe_2H^+]$ $[(p-FC_6H_4)_4B^-]$ (64.3 mg, 0.125 mMol) at room temperature. A yellow precipitate formed which was isolated by centrifugation of the reaction mixture and decanting of the mother liquor. The obtained precipitate was washed once more with fresh toluene and thereafter dried under vacuum. Yield was quantitative assuming the solid had composition $[(C_4Me_4P)_2ZrMe^+]$ $[(p-FC_6H_4)_4B^-]$. The resulting material was used as a catalyst in olefin polymerizations. It is moderately well soluble in bromobenzene and its $^1$H-NMR in $d^5$-bromobenzene shows only traces of free $PhNMe_2$.

XXXVI $(C_4Me_4P)(C_5H_5)ZrMe_2$, XXVII, (42 mg, 0.125 mMol) was dissolved in toluene/hexane (½) and reacted with $[PhNMe_2H^+][(p-FC_6H_4)_4B^-]$ (64.3 mg, 0.125 mMol) at room temperature. A brown sticky compound formed immediately. This was treated with hexane to afford a yellow-green solid which was isolated by centrifugation of the reaction mixture and decanting of the mother liquor. The obtained precipitate was washed twice with fresh hexane and thereafter dried under vacuum. Yield was quantitative assuming the solid had composition $[(C_4Me_4P)(C_5H_5)ZrMe^+][(p-FC_6H_4)_4B^-]$. The resulting material was used as a catalyst in olefin polymerizations.

EXAMPLE C

Polymerization experiments.

Experiment 1

Catalyst XXXIV, 0.125 mMol (starting from 50 mg $(C_4Me_4P)_2ZrMe_2$,XXVI) was taken up in 5 ml of bromobenzene and charged to a 25 ml autoclave. At a temperature of 45° C. the autoclave was charged with 600 kPa of propene and connected to an approximately 1.5 l. supply vessel also charged with 600 kPa propene at 45° C. Initial decrease in propene pressure were corrected by repressuring autoclave and supply vessel after ca. 10 minutes to 600 kPa. Thereafter, during the reaction the pressure and the decrease in pressure were recorded continuously. After 1.5 hours the reaction was stopped. Analysis and measuring of the autoclave contents showed that 2 ml of organic liquid had been formed which were characterized as atactic propene polymers of low molecular weight, $M_2=120$ ($^1$H-NMR).

Experiment 2

Catalyst XXXV, 0.125 mMol (prepared starting from 50 mg $(C_4Me_4P)_2ZrMe_2$, XXVI) was taken up in 5 ml of bromobenzene and charged to a 25 ml autoclave. At a temperature of 45° C. the reactor was charged with 600 kPa of propene and connected to an approximately 1.5 l. supply vessel also charged with 600 kPa propene at 45° C. During the reaction the pressure and the decrease in pressure were recorded continuously. After 13 minutes the reaction was stopped. Analysis and measuring of the autoclave contents showed the formation of 0.5 ml of atactic propene polymers of low molecular weight, $M_n=180$ ($^1$H-NMR).

Experiment 3

Catalyst XXXV, 0.125 mMol (prepared starting from 50 mg $(C_4Me_4P)_2ZrMe_2$, XXVI) was taken up in 1 ml of toluene and subsequently 4 ml of toluene solution containing 10% MAO were added. The solution was charged to a 25 ml autoclave. At 45° C. 600 kPa of propene were charged to the autoclave and connected to an approximately 1.5 l. supply vessel also charged with 600 kPa propene at 45° C. Initial decrease in propene pressure were corrected by repressuring autoclave and supply vessel after ca. 10 minutes to 600 kPa. Thereafter, during the reaction the pressure and the decrease in pressure were recorded continuously. After 52 minutes the reaction was stopped. Analysis and measuring of the autoclave contents showed the formation of 8 ml of atactic propene polymers of low molecular weight, $M_n=690$ ($^1$H-NMR).

Experiment 4

Similar to Exp. 3 except that the reaction was stopped after 40 minutes. Yield 5 ml of atactic propene polymers of low molecular weight, $M_n=460$ ($^1$H-NMR).

Experiment 5

Similar to Exp. 3 except that the reactor and supply vessel were charged with 3 bar of ethylene instead of 600 kPa propene. Furthermore, initial drop in pressure was not corrected. After 15 minutes the reaction was stopped. Inspection of the autoclave contents showed that a white powder, polyethylene, had formed. It was isolated by filtration, yield 1.15 g, with melting point 119° C.

Experiment 6

Similar to Exp. 5 except that before ethylene was charged 2 ml of styrene were added to the autoclave. After 13 minutes the reaction was terminated and the autoclave contents analyzed. 2.0 gr of solid products and 0.5 ml of soluble products had formed which $^1$H-NMR and $^{13}$C-NMR spectra showed the presence of both styrene and ethylene. The solid product showed a melting point of 108° C.

Experiment 7

Catalyst XXXV, 160 mg, 0.25 mMol (prepared starting from 100 mg $(C_4Me_4P)_2ZrMe_2$ according to the procedure described above), was taken up in 6 ml of toluene and 4 ml of a toluene solution containing 10% MAO. To a 1 ltr autoclave, equipped with a magnetic stirring and catalyst injection device, 180 ml toluene and 2 ml 10% MAO in toluene were added. The contents were heated to 45° C. and pressurized with 600 kPa of propene under continuous stirring. After 15 minutes 2 ml of the 10% MAO solution in toluene were injected via the catalyst injection system and the injection system was subsequently washed with 10 ml of fresh toluene. Both fraction were added to the autoclave.

Hereafter the catalyst system was used to inject the catalyst XXXV/MAO mixture. During the experiments propene was continuously fed to the reactor to keep the pressure at 600 kPa. After 26 minutes the reaction was terminated. Analysis of the reactor contents showed the formation of 54 gr of atactic propene polymer of low molecular weight, $M_n=1000$ ($^1$H-NMR).

Experiment 8

Similar to Exp. 6 except that 600 kPa of propene were charged to the autoclave in stead of 300 kPa ethene. After 20 minutes the reaction was terminated and the reactor contents analyzed. The reaction afforded 6 ml of product which appeared to be a copolymer of propene and styrene. $M_n=750$ ($^1$H-NMR, $^{13}$C-NMR).

Experiment 9

Catalyst XXXV, 0.025 mMol (starting from 10 mg $(C_4Me_4P)_2ZrMe_2$, XXVI) were taken up in 0.5 ml of bromobenzene in a glass mini reactor. To the reactor were added 0.1 ml of hexene-1 at room temperature. Within 2 minutes complete conversion of hexene-1 was observed with concomitant formation of poly(hexene-1) of low molecular weight, $M_n=170$ ($^1$H-NMR).

Experiment 10

Catalyst XXXV in combination with MAO, similar to Exp. 3, was dissolved in 40 ml of toluene in a glass Schlenk vessel and 20 ml hexene-1. After 60 hours at room temperature evaporation of the reaction volatiles 5 g of oligomeric poly-hexene-1 was recovered, $M_n=650$ ($^1$H-NMR).

Experiment 11

A 1 ltr autoclave (see Exp. 7) containing 200 ml of toluene and 4 ml of a toluene solution containing 10% MAO, was charged with 300 Kpa of ethene at 45° C. The system was allowed to reach equilibrium while the pressure was kept at 300 kPa. Subsequently, ethylene supply was shut of and $(C_4Me_4P)_2ZrCl_2$, I, 0.01 mMol, dissolved in 10 ml of toluene were added to the autoclave by means of the catalyst injection system. After 7 minutes the reaction was stopped and after release of excess ethylene, the autoclave contents isolated. 4 Grams of a white powder, which was found to be polyethylene (m.p. 115.5° C.), were obtained.

Experiment 12

Similar to Exp. 11 except that $(C_4Me_4P)(C_5H_5)ZrCl_2$, II, was used as catalyst precursor instead of $(C_4Me_4P)_2ZrCl_2$, I, and the reaction was run at 60° C. After 4 minutes the reaction afforded 4.1 g of polyethylene.

Experiment 13

Similar to Exp. 11 except that the catalyst precursor was $[W(CO)_4(C_4Me_4P)_2]ZrCl_2$, V, the olefin feed was 600 kPa of propene, and the reaction temperature was 50° C. Atactic propene polymer were recovered from the reaction mixture ($M_n=3.000$, activity is 10.000 mMol propene/mMol "Zr"/hr).

Experiment 14

Similar to Exp. 3 but instead of MAO, i-$Bu_6Al_4O_3$ was added (same ratio of Zr:Al in both cases). The reaction afforded after 4 hours 1.5 ml of propene oligomers ($M_n$ not determined).

Experiment 15

Similar to Exp. 7 but instead of catalyst XXXV catalyst XXXVI (0.25 mMol prepared from 85 mg $(C_4Me_4P)(C_5H_5)ZrMe_2$, XXVII, and 128 mg of borate) was used. After 2 hours 12 g atactic propene oligomer was formed with mol. weight of 380.

Experiment 16

A 1 ltr autoclave (see Exp. 7) containing 200 ml of toluene and 3.5 ml of a toluene solution containing 10% MAO, was charged with 600 kPa of propene at 45° C. The system was allowed to reach equilibrium while the pressure was kept at 600 kPa. Subsequently, $(2,5-Ph_2C_4H_2P)_2ZrCl_2$, VI, 0.01 mMol, dissolved in 10 ml of toluene, were added to the autoclave by means of the catalyst injection system. After 14 minutes the reaction was stopped by release of excess propylene. The autoclave contents were isolated and weighed. Comparison of the weight of the reactor contents before and after the polymerization reaction showed the formation of 38 g of product which is an atactic propene polymer (with molecular weight >50.000).

Experiment 17

Similar to Exp. 16 except that $(2,5-Ph_2C_4H_2P)_2ZrCl_2$, VI, was replaced with an equimolar amount of $(2,5-Ph_2C_4H_2P)(C_5H_5)ZrCl_2$, VII. Reaction time was 30 minutes and yield 31 g of atactic propene polymer of molecular weight 1700.

Experiment 18

In a 25 ml autoclave $(C_4Me_4P)_2ZrCl_2$, I, 0.01 mMol, was dissolved in 10 ml of toluene. To this solution MAO-on-$SiO_2$ (purchased from Witco, containing 17% Al) were added and this mixture stirred for 5 minutes by means of a magnetic stirring bar. During this time the solution discolorized and the heterogeneous phase became dark yellow. Subsequently the autoclave was pressurized with 600 kPa of propene and warmed to 45° C. After 48 minutes the reaction was terminated by releasing the propene pressure. The reaction contents were treated with a small amount of water, filtrated to remove the solids, dried over $MgSO_4$, and the volatiles removed under vacuo. Yield (determined by weighing reactor contents before and after reaction) 2.7 g of a propene polymer with molecular weight of 610 (determined by $^1$H-NMR).

Experiment 19

17% Al was replaced with one containing 24.% Al. Yield after 1 hour 25 minutes 2.6 g propene polymer of molecular weight 910.

Experiment 20

In a 1 ltr autoclave 120 ml of toluene containing $(C_4Me_4P)_2ZrCl_2$, I, 0.02 mMol, and 1.12 g of MAO-on-$SiO_2$ were introduced under vacuum by means of a syringe. The syringe was rinsed with another 100 ml of toluene which were also introduced in the reactor. Subsequently the reactor was pressurized with 600 kPa of propene and heated to 45° C. After 2 hours and 40 minutes the reaction was terminated by release of the propene pressure and the product worked up by filtration and evaporating of the volatiles under vacuum. Yield 5.6 g of polypropylene with a molecular weight of 1470

Experiment 21

In a 25 ml autoclave catalyst XXXV, 0.125 mMol, was stirred in 10 ml of toluene with MAO-on-$SiO_2$ (24.5% Al), 2.8 g (Zr:Al=1:200). The autoclave was charged with 600 kPa of propene and heated till 45° C. After 26 minutes the reaction was stopped and the product isolated. Yield: 2.2 g of polypropylene with molecular weight 350.

Experiment 22

Similar to Exp. 20 except that $(C_4Me_4P)_2ZrCl_2$, I, was replaced with catalyst XXXV, 0.25 mMol and 1.38 g of MAO-on-$SiO_2$ (24.5% Al) (Zr:Al=1:50) was used. After 1 hour and 5 minutes work up of the reactor contents afforded 13.25 g of polypropylenes with molecular weight 660.

Experiment 23

Similar to Exp. 18 except that $(C_4Me_4P)_2ZrCl_2$, I, was replaced with $(3,4-Me_2C_4H_2P)_2ZrCl_2$, III. After 35 minutes stirring of the reaction mixture was stopped to allow the solids to settle. After settling of the solids the clear solution was decanted and worked up. This afforded 0.7 g of propene oligomers with molecular weight 550. The settled solids were suspended in 10 ml of toluene and this suspension again exposed to 600 kPa of propene. After 45 minutes similar work up of the reaction mixture as described for the first polymerization afforded 0.4 g of propene oligomers with molecular weight 550. Treating the solids for the third time with propene as described heretofore and complete work up of the reaction contents after 25 minutes afforded 0.6 g of propene oligomers with molecular weight of 1300.

Experiment 24

In a 1 ltr. autoclave toluene was introduced containing 5 mMol of MAO. The reactor was charged with 100 kPa of ethylene and warmed till 45° C. After equilibration of the system, $(3,4-Me_2C_4H_2P)_2ZrCl_2$, III, 0.01 mMol, dissolved in toluene was introduced in the reactor by means of a catalyst injection system. Total amount of toluene is 220 ml. After 5 minutes the reaction was stopped and produced polyethylene recovered by filtration of the reactor contents. Yield 1.9 g.

Experiment 25

Similar to Exp. 24 except that $(3,4-Me_2C_4H_2P)_2ZrCl_2$, III, was replaced with $(3,4-Me_2C_4H_2P)(C_5H_5)ZrCl_2$, IV. The reaction afforded 6.1 g. of polyethylene.

Experiment 26

To a 1 l autoclave containing 240 ml of toluene containing 10 mMol of MAO under 580 kPa of propene at 40° C., were charged 10 ml of toluene containing 0.02 mMol of $(Me_4C_4AS)(C_5H_5)ZrCl_2$, VIII, by means of a catalyst injection system. The reaction was terminated by venting excess propene and subsequently the product was isolated by evaporating of the volatiles. The reaction afforded atactic polypropylenes with molecular weight >10.000 and showed a turnover number 3000 mMol/mMol.h.

Experiment 27

Similar to Exp. 16 except that $(2,5-Ph_2C_4H_2P)_2ZrCl_2$, VI, was replaced with an equimolar amount of $(2,5-Ph_2-3,4-Me_2C_4)_2ZrCl_2$, IX. Reaction time was 30 minutes and yield 7 g of atactic propene polymer of molecular weight 450. Turnover number=33.000 mol/mol.h.

Experiment 28

Similar to Exp. 16 except that $(2,5-Ph_2C_4H_2P)_2ZrCl_2$, VI, was replaced with an equimolar amount of $(Ph_4C_4P)_2ZrCl_2$, XI. Reaction time was 30 minutes and the reaction yielded only traces of propene polymer which was not further analyzed.

Experiment 29

Similar to Exp. 16 except that $(2,5-Ph_2C_4H_2P)_2ZrCl_2$, VI, was replaced with an equimolar amount of $(2,5-Ph_2-3,4-Me_2C_4P)_2ZrCl_2$, X. Reaction time was 10 minutes and yield 12.5 g of atactic propene polymer of molecular weight 20.000. Turnover number=180.000 mol/mol.h.

Experiment 30

Similar to Exp. 16 except that $(2,5-Ph_2C_4H_2P)_2ZrCl_2$, VI, was replaced with an equimolar amount of $(2-Me-5-PhC_4H_2P)_2ZrCl_2$, XII. Reaction time was 26 minutes and yield 38 g of atactic propene polymer of molecular weight 6.700. Turnover number=200.000 mol/mol.h.

Experiment 31

Similar to Exp. 16 except that $(2,5-Ph_2C_4H_2P)_2ZrCl_2$, VI, was replaced with an equimolar amount of $(2-(3,5-t-Bu_2-4-OMeC_6H_2)-5-MeC_4H_2P)_2ZrCl_2$, XIII. Reaction time was 55 minutes and yield 50 g of atactic propene polymer of molecular weight 7.500. Turnover number=120.000 mol/mol.h.

Experiment 32

Similar to Exp. 16 except that $(2,5-Ph_2C_4H_2P)_2ZrCl_2$, VI, was replaced with an equimolar amount of $(C_{17}H_{12}P)_2ZrCl_2$, XIV. Reaction time was 30 minutes and yield 14 g of atactic propene polymer of molecular weight >50.000. Turnover number=70.000 mol/mol.h.

Experiment 33

Similar to Exp. 16 except that $(2,5-Ph_2C_4H_2P)_2ZrCl_2$, VI, was replaced with an equimolar amount of $(2,5-n-Pr_2C_4H_2P)_2ZrCl_2$, XV. Reaction time was 10 minutes and yield 1.2 g of atactic propene polymer of molecular weight 1.600. Turnover number=17.500 mol/mol.h.

Experiment 34

Similar to Exp. 16 except that $(2,5-Ph_2C_4H_2P)_2ZrCl_2$, VI, was replaced with an equimolar amount of $(3,4-Me_2C_4H_2P)_2ZrCl_2$, III. Reaction time was 15 minutes and the reaction yielded only traces of propene polymer which was not further analyzed.

Experiment 35

Similar to Exp. 16 except that $(2,5-Ph_2C_4H_2P)_2ZrCl_2$, VI, was replaced with an equimolar amount of $(2,5-t-Bu_2C_4H_2P)(C_5H_5)ZrCl_2$, XVI. Reaction time was 45 minutes and the reaction yielded 9.5 g atactic propene oligomers of molecular weight 1.400. Turnover number=17.000 mol/mol.h.

Experiment 36

Similar to Exp. 16 except that $(2,5-Ph_2C_4H_2P)_2ZrCl_2$, VI, was replaced with an equimolar amount of $(2,5-c-Pe_2C_4H_2P)_2ZrCl_2$, XVII. Reaction time was 10 minutes and the reaction yielded 17.5 g of atactic propene polymer of molecular weight 1.500. Turnover number=250.000 mol/mol.h.

Experiment 37

In a 1 ltr autoclave 120 ml of toluene containing $(2,5-Ph_2C_4H_2P)_2ZrCl_2$, VI, 0.01 mMol, and 1.12 g of MAO-on-$SiO_2$ (purchased from Witco, containing 17% Al) were introduced under vacuum by means of a syringe. The syringe was rinsed with another 100 ml of toluene which were also introduced in the reactor. Subsequently the reactor was pressurized with 600 kPa of propene and heated to 45° C. After 48 minutes the reaction was terminated by release of the propene pressure and the product worked up by filtration and evaporating of the volatiles under vacuum. Yield 14.5 g of polypropylene with a molecular weight of 4.600. Turnover number=43.000 mol/mol.h.

Experiment 38

Similar to Exp. 18 except that $(C_4Me_4P)_2ZrCl_2$, I, was replaced with $(C_4Me_4P)(C_5H_5)ZrCl_2$, II. After 27 minutes 2.4 g of atactic propene polymer with molecular weight 470 were formed. Turnover number=12.400 mol/mol.h.

Experiment 39

Similar to Exp. 18 except that $(C_4Me_4P)_2ZrCl_2$, I, was replaced with $(3,4-Me_2C_4H_2P)(C_5H_5)ZrCl_2$, IV. After 45 minutes the yield of the reaction was 1.1 g of polypropylene. Turnover number=3.500 mol/mol.h.

Experiment 40

Similar to Exp. 16 except that propene was replaced with 300 kPa of ethylene. The reaction time was 5 minutes and the yield 7.2 g of polyethylene. Turnover number=310.000.

Experiment 41

Similar to Exp. 16 except that $(2,5\text{-Ph}_2C_4H_2)_2ZrCl_2$, VI, was replaced with $(Me_4C_4P)_2ZrCl_2$, I. After one hour the reaction afforded only traces of polypropylene which was not characterized further.

Experiment 42

Similar to Exp. 16 except that $(2,5\text{-Ph}_2C_4H_2P)_2ZrCl_2$, VI, was replaced with an equimolar amount of $(C_{20}H_{16}N)(C_5H_5)ZrCl_2$, XVIII. Reaction time was 50 minutes and the reaction yielded 31 g of atactic, highly branched propene polymer of molecular weight >10,000. Turnover number= 85,000 mol/mol.h.

Experiment 43

Similar to Exp. 16 except that $(2,5\text{-Ph}_2C_4H_2P)_2ZrCl_2$.VI. was replaced with an equimolar amount of $(C_{20}H_{16}N)_2ZrCl_2$, XIX. Reaction time was 60 minutes and the reaction yielded 8.5 g of atactic, highly branched propene polymer of molecular weight 3,000. Turnover number=20,000 mol/ mol.h.

Experiment 44

Similar to Exp. 16 except that $(2,5\text{-Ph}_2C_4H_2P)_2ZrCl_2$, VI, was replaced with an equimolar amount of $(2,5\text{-i-Pr}_2C_4H_2P)_2ZrCl_2$, XVIIA. Reaction time was 30 minutes and the reaction yielded 17.0 g of atactic propene oligomers with molecular weight 1,400. Turnover number=79,000.

A summary of the above polymerization experiments is given in Table 1.

Experiments 45–50

Copolymerization of ethylene with octene-1 catalyzed by $(2,5\text{-Ph}_2C_4H_2P)_2ZrCl_2$, VI.

The polymerization reactions were performed according to the following procedure:

Toluene and octene were introduced in a 1 l autoclave and to the mixture 5.0 mmol of MAO dissolved in toluene was added. Subsequently the mixture was heated to the reaction temperature while ethylene was supplied at constant pressure. After equilibration 0.01 mmol of catalyst precursor $(2,5\text{-Ph}_2C_4H_2P)_2ZrCl_2$, VI, was added to the reactor contents by means of a catalyst injection device. During polymerization ethylene was supplied to maintain the original pressure. After reaction the reaction contents were poured into methanol, isolated by centrifugation, dried at 70° C. under vacuum, weighed, and characterized. The polymerization experiments and the reaction parameters and results are summarized in Table 2.

Experiments 51–56

Styrene polymerization experiments

The reactions were performed according to the following procedure unless stated otherwise:

To a solution of 0.01 mmol of phospholyl $TiCl_3$ in 5 ml of toluene was added 5.00 mmol of MAO (3.35 ml, 10% w Al in toluene) at room temperature. This solution was warmed to 60° C. and after stirring for 10 minutes 5 ml of cold purified styrene was added. The polymerization was terminated by pouring the reaction into a 5% HCl/methanol solution. The precipitate was isolated by centrifugation, washed with methanol and dried in vacuo to a constant weight. The products were characterized as syndiotactic polystyrenes on the basis of NMR and melting point.

The results, including the melting temperatures of the products, are listed in Table 3.

EXAMPLE D

Oligomerization and co-oligomerization experiments. Experiments 57–61, Oligomerization of ethylene.

The heterocyclopentadienyl zirconium complexes used in these five experiments were: XXVI, XXXII, XXVII, XXX and XXXIII, respectively.

In all five experiments a 500 ml autoclave was charged with 90 ml of toluene, containing 0.05 mmol of $[Bu_3NH^+]$ $[B_{11}CH_{12}{-}]$. The reactor contents was heated to 90° C. and subsequently pressurized with 1000 kPa of ethylene. Hereafter, the heterocyclopentadienyl zirconium complex, dissolved in 10 ml of toluene, was injected. During the reaction constant pressure was maintained by continuous supply of ethylene. At the end of the (predetermined) reaction time, the reaction was terminated by water injection. Yields were determined by monitoring ethylene uptake, product distribution was determined by gas-liquid chromatography. The outcomes of the reactions are given in Table 4.

Experiment 62. Co-oligomerization of ethylene with 1-pentene.

The heterocyclopentadienyl zirconium complex used in this experiment was XXVI.

The procedure was identical to that described in Exp. 27 except that the total amount of comonomer, 457 mmol of 1-pentene, was charged together with the solvent, 90 ml of toluene, at the start of the experiment. The outcome of the reaction is given in Table 5.

TABLE 1

Polymerization experiments 1–44

| Exp | Cat. | Cocat | 3rd comp. | Feed | Turn-over[a] | Mol. Weight (Mn) |
|---|---|---|---|---|---|---|
| 1 | XXXIV | | — | Propene | −200 | 120 |
| 2 | XXXV | | — | Propene | −400 | 180 |
| 3 | XXXV | | MAO | Propene | 1,300 | 690 |
| 4 | XXXV | | MAO | Propene | −1,200 | 460 |
| 5 | XXXV | | MAO | Ethene | −1,800 | b) |
| 6 | XXXV | | MAO | Ethene/Styrene | | c) |
| 7 | XXXV | | MAO | Propene | 12,000 | 1,000 |
| 8 | XXXV | | MAO | Propene/Styrene | | 750[d] |
| 9 | XXXV | | MAO | Hexene-1 | −10,000 | 170 |
| 10 | XXXV | | MAO | Hexene-1 | −35 | 650 |
| 11 | I | MAO | — | Ethene | 120,000 | e) |
| 12 | II | MAO | — | Ethene | 220,000 | — |

TABLE 1-continued

Polymerization experiments 1-44

| Exp | Cat. | Cocat | 3rd comp. | Feed | Turn-over[a] | Mol. Weight (Mn) |
|---|---|---|---|---|---|---|
| 13 | V | MAO | — | Propene | 3,000 | 10,000 |
| 14 | XXXV | | IBAO | Propene | 70 | |
| 15 | XXXVI | | MAO | Propene | 2,400 | 380 |
| 16 | VI | MAO | — | Propene | 360,000 | >50,000 |
| 17 | VII | MAO | — | Propene | 140,000 | 1,700 |
| 18 | I | MAO/SiO$_2$ | — | Propene | 8,000 | 610 |
| 19 | I | MAO/SiO$_2$ | — | Propene | 4,500 | 910 |
| 20 | I | MAO/SiO$_2$ | — | Propene | 2,500 | 1470 |
| 21 | XXXV | MAO/SiO$_2$ | — | Propene | 850 | 330 |
| 22 | XXXV | | MAO/SiO$_2$ | Propene | 1,200 | 660 |
| 23 | III | MAO/SiO$_2$ | | Propene | | 550 |
| | | MAO/SiO$_2$ | | Propene | | 610 |
| | | MAO/SiO$_2$ | | Propene | | 610 |
| 24 | III | MAO | — | Ethene | 85,000 | |
| 25 | IV | MAO | — | Ethene | 260,000 | |
| 26 | VIII | MAO | — | Propene | 3,000 | >10,000 |
| 27 | IX | MAO | — | Propene | 33,000 | 450 |
| 28 | XI | MAO | — | Propene | trace | — |
| 29 | X | MAO | — | Propene | 180,000 | 20,000 |
| 80 | XII | MAO | — | Propene | 200,000 | 6,700 |
| 81 | XIII | MAO | — | Propene | 120,000 | 7,500 |
| 32 | XIV | MAO | — | Propene | 70,000 | >50,000 |
| 33 | XV | MAO | — | Propene | 17,500 | 1,600 |
| 34 | III | MAO | — | Propene | traces | — |
| 35 | XVI | MAO | — | Propene | 17,000 | 1,400 |
| 36 | XVII | MAO | — | Propene | 250,000 | 1,500 |
| 37 | VI | MAO/SiO$_2$ | — | Propene | 43,000 | 4,600 |
| 38 | II | MAO/SiO$_2$ | — | Propene | 12,400 | 470 |
| 39 | IV | MAO/SiO$_2$ | — | Propene | 3,500 | — |
| 40 | VI | MAO | — | Ethene | 310,000 | — |
| 41 | I | MAO | — | Propene | trace | — |
| 42 | XVIII | MAO | — | Propene | 85,000 | >10,000 |
| 48 | XIX | MAO | — | Propene | 20,000 | 3,000 |
| 44 | XVIIA | MAO | — | Propene | 79,000 | 1,400 |

[a] Mol/Mol. h.
[b] PE m.p. = 119° C.
[c] PE-copolymer m.p. = 108° C.
[d] PE-copolymer
[e] PE m.p. = 115° C.

TABLE 2

Ethylene-octene-1 copolymerization.

| Exp. | Toluene ml | Octene-1 g | Ethylene kPa | Temp. °C. | Time min. | Yield g | Ratio C$_2$/C$_8$ mol/mol |
|---|---|---|---|---|---|---|---|
| 45 | 150 | 40 | 40 | 70 | 8 | 9.6 | 0.5:1 |
| 46 | 150 | 40 | 100 | 30 | 10 | not det. | 0.6:1 |
| 47 | 150 | 40 | 300 | 71 | 5 | 13 | 2.1:1 |
| 48 | 210 | 10 | 300 | 70 | 6 | 26 | 6.2:1 |
| 49 | 210 | 10 | 300 | 30 | 6 | 21 | 6.6:1 |
| 50 | 210 | 10 | 300 | 10 | 6 | 16 | 4.6:1 |

TABLE 3

Styrene polymerizations

| Exp. | Catalyst | Reaction time (min.) | Yield (g) | t.o.f. (mol/mol. hr[c]) | M.p. (DSC) (°C.) |
|---|---|---|---|---|---|
| 51 | XX | 30 | 0.01 | 20 | |
| | | 90 | 0.05 | 30 | 260,266 |
| 52 | XXI | 30 | 0.01 | 20 | |
| | | 90 | 0.06 | 40 | 259,264 |
| 53 | XXII | 20 | 0.09 | 260 | |
| | | 30 | 0.12 | 230 | |
| | | 60 | 0.16 | 310[a] | 258,266 |
| 54 | XXIII | 60 | 0.04 | 40[b] | |
| 55 | XXIV | 60 | 0.03 | 30 | 256,265 |
| 56 | XXV | 120 | 1.50 | 720[d] | 253,264 |

Conditions: 0.01 mmol catalyst, 5.00 mmol MAO, 5 ml toluene, 5 ml styrene, 60° C.
[a] 0.005 mmol catalyst, 20 mmol MAO, 10 ml toluene.
[b] 0.0065 mmol catalyst, 3.25 mmol MAO.
[c] mol syndiotactic polystyrene/(mol catalyst. hr).
[d] 0.02 mmol catalyst, 10.0 mmol MAO, 10 ml toluene, 5 ml styrene, 25° C.

TABLE 4

Oligomerization

| Experiment | 57 | 58 | 59 | 60 | 61 |
|---|---|---|---|---|---|
| reaction time (min) | 30 | 30 | 6 | 26 | 24 |
| Ethene consumed (g) | 62 | 7 | 10 | 8 | 8 |
| Product C$_4$ olefin (g) | 0.7 | 0.8 | 0.04 | 0.1 | 0.3 |

TABLE 4-continued

| Oligomerization | | | | | |
|---|---|---|---|---|---|
| Product $C_8$, $C_{10}$ olefins (g) | 3.6 | 2.3 | 0.2 | 0.6 | 1.2 |
| hexene (g) | 1.0 | 0.8 | 0.06 | 0.2 | 0.4 |
| Product $C_{12+}$ olefins (g) | 57.7 | 3.9 | 9.7 | 7.3 | 6.5 |
| Distributions of hexenes (wt %) | | | | | |
| 1-hexene | 94.0 | 89.3 | 95.0 | 96.0 | 94.9 |
| 2-hexene | 5.7 | 10.3 | 5.0 | 3.7 | 4.5 |
| 2-ethyl-1-butene | 0.3 | 0.4 | 0.0 | 0.3 | 0.6 |

TABLE 5

| Co-oligomerization | |
|---|---|
| Experiment | 62 |
| reaction time (min) | 3 |
| Ethene consumed (g) | 8.2 |
| Product $C_4$ olefin (g) | 0.05 |
| Product $C_6$, $C_8$, $C_{10}$ olefins (g) | 0.2 |
| hexene (g) | 0.03 |
| Product $C_7$, $C_9$, $C_{11}$ olefins (g) | n.a. |
| heptene (g) | 0.07 |
| Product $C_{12+}$ olefins (g) | n.a. |
| Distributions of hexenes (wt %) | |
| 1-hexene | 95.5 |
| 2-hexene | 4.0 |
| 2-ethyl-1-butene | 0.5 |
| Distribution of heptenes (wt %) | |
| 1-heptene | 89.0 |
| 2-heptene | 4.0 |
| 2-ethyl-1-pentene | 7.0 | n.a. = not available yet.

What is claimed is:

1. A composition comprising
   (a) (2-R-5-R'$C_4H_2P$)$_a$M$Q_{n-a}$
   wherein R and R' are selected from the group consisting of bulky substituents or methyl, with at least one of R and R' being a bulky substituent, wherein the bulky substituent is selected from the group consisting of phenyl, o-tolyl, p-t-butyl phenyl, m-dichlorophenyl, 3,5-t-Bu$_2$-4-MeO$C_6H_2$, i-propyl, i-butyl, cyclopentyl, t-butyl, —C(CH$_3$)=CH$_2$, —Si(CH$_3$)$_3$, —N(C$_6$H$_5$)$_2$, —NH(C$_6$H$_5$)$_2^+$, —B(C$_6$H$_5$)$_2$ and —B(OC$_6$H$_5$)$_2$.

M is selected from the group consisting of Zr, Hf and Ti.

Q is selected from the group consisting of aryl, alkyl, alkenyl, alkaryl, alkylonyl, aryl oxyl, alkyl azanyl, arylazanyl, alkyl thiolyl, aryl thiolyl, alkyl phosphalyl, aryl phosphalyl, alkyl azanediyl and cyclodienyl, any of which have from 1 to 20 carbon atoms and may be further substituted with hydrogen, halogens, oxygen or sulphur, a=1 or 2; and n=valency of M; and (b) a cocatalyst.

2. A composition according to claim 1 where Q is Cl or CH$_3$.

3. A composition according to claim 1 wherein R is phenyl, i-propyl, t-butyl or cyclopentyl.

4. A composition according to claim 3 wherein R is t-butyl.

5. A composition according to claim 3 wherein R' is hydrogen, methyl or the same as R.

6. A composition according to claim 5 where a=2.

7. A composition according to claim 6 where M is Zr.

8. A composition according to claim 7 wherein the composition is selected from the group consisting of (2-5-di-cyclopentyl $C_4H_2P$)$_2$ZrCl$_2$, (2-5-di-t-butyl $C_4H_2P$)$_2$ZrCl$_2$, and (2-5-di-phenyl $C_4H_2P$)$_2$ZrCl$_2$.

9. A composition according to claim 5 selected from the group consisting of (2-CH$_3$-5-Ph$C_4H_2P$)ZrCl$_2$, and (2-CH$_3$,-5-Ph$C_4H_2P$)TiCl$_2$.

* * * * *